(12) United States Patent
Medico et al.

(10) Patent No.: US 6,551,991 B1
(45) Date of Patent: Apr. 22, 2003

(54) RECOMBINANT PROTEINS DERIVED FROM HGF AND MSP

(75) Inventors: Enzo Medico, L'Aquila (IT); Paolo Michieli, L'Aquila (IT); Chiara Collesi, L'Aquila (IT); Gianfranco Caselli, L'Aquila (IT); Paolo Comoglio, L'Aquila (IT)

(73) Assignee: Dompe' S.p.A., L'Aquila (IT)

( * ) Notice: Subject to any disclaimer, the term of this patent is extended or adjusted under 35 U.S.C. 154(b) by 0 days.

(21) Appl. No.: 09/600,991

(22) PCT Filed: Jan. 27, 1999

(86) PCT No.: PCT/EP99/00478

§ 371 (c)(1),
(2), (4) Date: Sep. 15, 2000

(87) PCT Pub. No.: WO99/38967

PCT Pub. Date: Aug. 5, 1999

(30) Foreign Application Priority Data

Jan. 30, 1999 (IT) ............................... MI98A0179

(51) Int. Cl.⁷ ................... A61K 38/00; A61K 31/44; A61K 14/00; A61K 38/18; C07K 16/00
(52) U.S. Cl. ................... 514/2; 530/300; 530/350; 530/388.22; 530/399; 530/402; 536/23.5; 536/23.1; 435/69.7
(58) Field of Search .............. 424/198.1; 435/69.1, 435/35, 7.1, 69.7; 530/399, 350, 402, 388.22, 300; 514/2, 12; 536/23.5, 23.1

(56) References Cited

U.S. PATENT DOCUMENTS 5,350,836 A * 9/1994 Kopchick et al.

FOREIGN PATENT DOCUMENTS

| WO | A1-9323541 | 11/1993 |
|---|---|---|
| WO | A2-9323550 | 11/1993 |
| WO | A1-9406456 | 3/1994 |

OTHER PUBLICATIONS

Gaudino et al., EMBO Journal, vol. 13, No. 15, pp. 3524–3532 (1994).

Hartmann et al., Proc. Nat'l Acad. Sci. USA, vol. 89, pp. 11574–11578 (1992).

Trusolino et al., FASEB Journal, vol. 12, No. 13, pp. 1267–1280 (1998).

Truselino, et al. 1998, FASEB J. 12(13):1267–1280, esp. p. 1274–1275.*

Danilkovich, A., et al (1999), J. Biol. Chem., 274(42):29937–29943; esp. Fig 4.*

* cited by examiner

*Primary Examiner*—Elizabeth Kemmerer
*Assistant Examiner*—Sandra Wegert
(74) *Attorney, Agent, or Firm*—Birch, Stewart, Kolasch & Birch, LLP

(57) ABSTRACT

Recombinant proteins deriving from recombination of structural domains deriving from the α subunits of HGF and/or MSP growth factors. The recombinant proteins of the present invention have biological activity, and protect cells from death (apoptosis) induced by chemotherapeutic drugs. These molecules can conveninently be used to prevent or to treat the toxic side effects of chemotherapeutic agents used in cancer therapy.

5 Claims, 19 Drawing Sheets

Figure 2A:
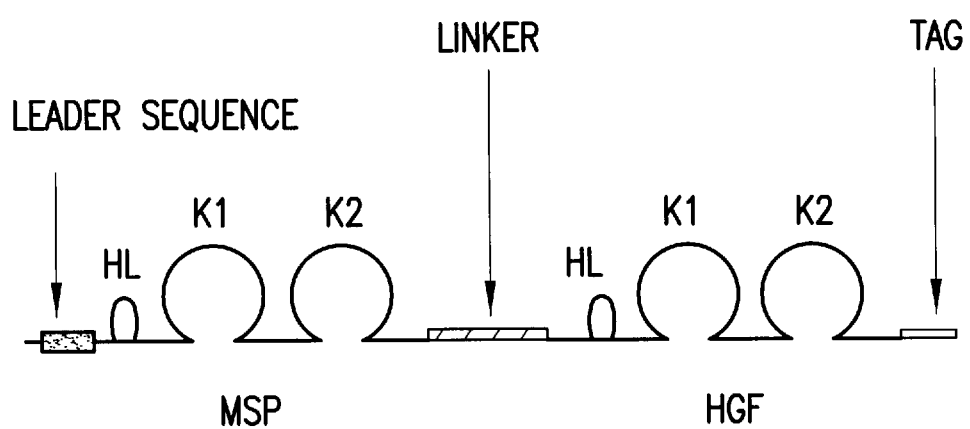

```
    ATGTGGGTGACCAAACTCCTGCCAGCCCTGCTGCTGCAGCATGTCCTCCTGCATCTCCTC
1   ---------+---------+---------+---------+---------+---------+   60
    TACACCCACTGGTTTGAGGACGGTCGGGACGACGACGTCGTACAGGAGGACGTAGAGGAG
1   M  W  V  T  K  L  L  P  A  L  L  L  Q  H  V  L  L  H  L  L     20
    CTGCTCCCCATCGCCATCCCCTATGCAGAGGGACAAAGGAAAAGAAGAAATACAATTCAT
61  ---------+---------+---------+---------+---------+---------+   120
    GACGAGGGGTAGCGGTAGGGGATACGTCTCCCTGTTTCCTTTTCTTCTTTATGTTAAGTA
21  L  L  P  I  A  I  P  Y  A  E  G  Q  R  K  R  R  N  T  I  H     40
    GAATTCAAAAAATCAGCAAAGACTACCCTAATCAAAATAGATCCAGCACTGAAGATAAAA
121 ---------+---------+---------+---------+---------+---------+   180
    CTTAAGTTTTTTAGTCGTTTCTGATGGGATTAGTTTTATCTAGGTCGTGACTTCTATTTT
41  E  F  K  K  S  A  K  T  T  L  I  K  I  D  P  A  L  K  I  K     60
    ACCAAAAAAGTGAATACTGCAGACCAATGTGCTAATAGATGTACTAGGAATAAAGGACTT
181 ---------+---------+---------+---------+---------+---------+   240
    TGGTTTTTTCACTTATGACGTCTGGTTACACGATTATCTACATGATCCTTATTTCCTGAA
61  T  K  K  V  N  T  A  D  Q  C  A  N  R  C  T  R  N  K  G  L     80
    CCATTCACTTGCAAGGCTTTTGTTTTTGATAAAGCAAGAAAACAATGCCTCTGGTTCCCC
241 ---------+---------+---------+---------+---------+---------+   300
    GGTAAGTGAACGTTCCGAAAACAAAAACTATTTCGTTCTTTTGTTACGGAGACCAAGGGG
81  P  F  T  C  K  A  F  V  F  D  K  A  R  K  Q  C  L  W  F  P     100
    TTCAATAGCATGTCAAGTGGAGTGAAAAAAGAATTTGGCCATGAATTTGACCTCTATGAA
301 ---------+---------+---------+---------+---------+---------+   360
    AAGTTATCGTACAGTTCACCTCACTTTTTTCTTAAACCGGTACTTAAACTGGAGATACTT
101 F  N  S  M  S  S  G  V  K  K  E  F  G  H  E  F  D  L  Y  E     120
    AACAAAGACTACATTAGAAACTGCATCATTGGTAAAGGACGCAGCTACAAGGGAACAGTA
361 ---------+---------+---------+---------+---------+---------+   420
    TTGTTTCTGATGTAATCTTTGACGTAGTAACCATTTCCTGCGTCGATGTTCCCTTGTCAT
121 N  K  D  Y  I  R  N  C  I  I  G  K  G  R  S  Y  K  G  T  V     140
    TCTATCACTAAGAGTGGCATCAAATGTCAGCCCTGGAGTTCCATGATACCACACGAACAC
421 ---------+---------+---------+---------+---------+---------+   480
    AGATAGTGATTCTCACCGTAGTTTACAGTCGGGACCTCAAGGTACTATGGTGTGCTTGTG
141 S  I  T  K  S  G  I  K  C  Q  P  W  S  S  M  I  P  H  E  H     160
```

FIG.1a-1

```
        AGCTATCGGGGTAAAGACCTACAGGAAAACTACTGTCGAAATCCTCGAGGGGAAGAAGGG
481     ---------+---------+---------+---------+---------+---------+    540
        TCGATAGCCCCATTTCTGGATGTCCTTTTGATGACAGCTTTAGGAGCTCCCCTTCTTCCC
161      S  Y  R  G  K  D  L  Q  E  N  Y  C  R  N  P  R  G  E  E  G    180

GGACCCTGGTGTTTCACAAGCAATCCAGAGGTACGCTACGAAGTCTGTGACATTCCTCAG
541     ---------+---------+---------+---------+---------+---------+    600
        CCTGGGACCACAAAGTGTTCGTTAGGTCTCCATGCGATGCTTCAGACACTGTAAGGAGTC
181      G  P  W  C  F  T  S  N  P  E  V  R  Y  E  V  C  D  I  P  Q    200

TGTTCAGAAGTTGAATGCATGACCTGCAATGGGGAGAGTTATCGAGGTCTCATGGATCAT
601     ---------+---------+---------+---------+---------+---------+    660
        ACAAGTCTTCAACTTACGTACTGGACGTTACCCCTCTCAATAGCTCCAGAGTACCTAGTA
201      C  S  E  V  E  C  M  T  C  N  G  E  S  Y  R  G  L  M  D  H    220

ACAGAATCAGGCAAGATTTGTCAGCGCTGGGATCATCAGACACCACACCGGCACAAATTC
661     ---------+---------+---------+---------+---------+---------+    720
        TGTCTTAGTCCGTTCTAAACAGTCGCGACCCTAGTAGTCTGTGGTGTGGCCGTGTTTAAG
221      T  E  S  G  K  I  C  Q  R  W  D  H  Q  T  P  H  R  H  K  F    240

TTGCCTGAAAGATATCCCGACAAGGGCTTTGATGATAATTATTGCCGCAATCCCGATGGC
721     ---------+---------+---------+---------+---------+---------+    780
        AACGGACTTTCTATAGGGCTGTTCCCGAAACTACTATTAATAACGGCGTTAGGGCTACCG
241      L  P  E  R  Y  P  D  K  G  F  D  D  N  Y  C  R  N  P  D  G    260

CAGCCGAGGCCATGGTGCTATACTCTTGACCCTCACACCCGCTGGGAGTACTGTGCAATT
781     ---------+---------+---------+---------+---------+---------+    840
        GTCGGCTCCGGTACCACGATATGAGAACTGGGAGTGTGGGCGACCCTCATGACACGTTAA
261      Q  P  R  P  W  C  Y  T  L  D  P  H  T  R  W  E  Y  C  A  I    280

AAAACATGCGCTGACAATACTATGAATGACACTGATGTTCCTTTGGAAACAACTGAATGC
841     ---------+---------+---------+---------+---------+---------+    900
        TTTTGTACGCGACTGTTATGATACTTACTGTGACTACAAGGAAACCTTTGTTGACTTACG
281      K  T  C  A  D  N  T  M  N  D  T  D  V  P  L  E  T  T  E  C    300

ATCCAAGGTCAAGGAGAAGGCTACAGGGGCACTGTCAATACCATTTGGAATGGAATTCCA
901     ---------+---------+---------+---------+---------+---------+    960
        TAGGTTCCAGTTCCTCTTCCGATGTCCCCGTGACAGTTATGGTAAACCTTACCTTAAGGT
301      I  Q  G  Q  G  E  G  Y  R  G  T  V  N  T  I  W  N  G  I  P    320

TGTCAGCGTTGGGATTCTCAGTATCCTCACGAGCATGACATGACTCCTGAAAATTTCAAG
961     ---------+---------+---------+---------+---------+---------+    1020
        ACAGTCGCAACCCTAAGAGTCATAGGAGTGCTCGTACTGTACTGAGGACTTTTAAAGTTC
321      C  Q  R  W  D  S  Q  Y  P  H  E  H  D  M  T  P  E  N  F  K    340

TGCAAGGACCTACGAGAAAATTACTGCCGAAATCCAGATGGGTCTGAATCACCCTGGTGT
1021    ---------+---------+---------+---------+---------+---------+    1080
        ACGTTCCTGGATGCTCTTTTAATGACGGCTTTAGGTCTACCCAGACTTAGTGGGACCACA
341      C  K  D  L  R  E  N  Y  C  R  N  P  D  G  S  E  S  P  W  C    360

TTTACCACTGATCCAAACATCCGAGTTGGCTACTGCTCCCAAATTCCAAACTGTGATATG
1081    ---------+---------+---------+---------+---------+---------+    1140
        AAATGGTGACTAGGTTTGTAGGCTCAACCGATGACGAGGGTTTAAGGTTTGACACTATAC
361      F  T  T  D  P  N  I  R  V  G  Y  C  S  Q  I  P  N  C  D  M    380
```

FIG.1a-2

```
      TCACATGGACAAGATTGTTATCGTGGGAATGGCAAAAATTATATGGGCAACTTATCCCAA
1141  ------------+---------+---------+---------+---------+---------+  1200
      AGTGTACCTGTTCTAACAATAGCACCCTTACCGTTTTTAATATACCCGTTGAATAGGGTT
381   S  H  G  Q  D  C  Y  R  G  N  G  K  N  Y  M  G  N  L  S  Q   400

ACAAGATCTGGACTAACATGTTCAATGTGGGACAAGAACATGGAAGACTTACATCGTCAT
1201  ------------+---------+---------+---------+---------+---------+  1260
      TGTTCTAGACCTGATTGTACAAGTTACACCCTGTTCTTGTACCTTCTGAATGTAGCAGTA
401   T  R  S  G  L  T  C  S  M  W  D  K  N  M  E  D  L  H  R  H   420

ATCTTCTGGGAACCAGATGCAAGTAAGCTGAATGAGAATTACTGCCGAAATCCAGATGAT
1261  ------------+---------+---------+---------+---------+---------+  1320
      TAGAAGACCCTTGGTCTACGTTCATTCGACTTACTCTTAATGACGGCTTTAGGTCTACTA
421   I  F  W  E  P  D  A  S  K  L  N  E  N  Y  C  R  N  P  D  D   440

GACGCTCATGGACCCTGGTGCTACACGGGAAATCCACTCATTCCTTGGGATTATTGCCCT
1321  ------------+---------+---------+---------+---------+---------+  1380
      CTGCGAGTACCTGGGACCACGATGTGCCCTTTAGGTGAGTAAGGAACCCTAATAACGGGA
441   D  A  H  G  P  W  C  Y  T  G  N  P  L  I  P  W  D  Y  C  P   460

ATTTCTCGTTGTGAAGGTGATACCACACCTACAATAGTCAATTTAGACCATCCCGTAATA
1381  ------------+---------+---------+---------+---------+---------+  1440
      TAAAGAGCAACACTTCCACTATGGTGTGGATGTTATCAGTTAAATCTGGTAGGGCATTAT
461   I  S  R  C  E  G  D  T  T  P  T  I  V  N  L  D  H  P  V  I   480

TCTTGTGCCAAAACGAAACAATTGCGAGTTGTAAATGGGATTCCAACACGAACAAACATA
1441  ------------+---------+---------+---------+---------+---------+  1500
      AGAACACGGTTTTGCTTTGTTAACGCTCAACATTTACCCTAAGGTTGTGCTTGTTTGTAT
481   S  C  A  K  T  K  Q  L  R  V  V  N  G  I  P  T  R  T  N  I   500

GGATGGATGGTTAGTTTGAGATACAGAAAATAAACATATCTGCGGAGGATCATTGATAAAG
1501  ------------+---------+---------+---------+---------+---------+  1560
      CCTACCTACCAATCAAACTCTATGTCTTTATTTGTATAGACGCCTCCTAGTAACTATTTC
501   G  W  M  V  S  L  R  Y  R  N  K  H  I  C  G  G  S  L  I  K   520

GAGAGTTGGGTTCTTACTGCACGACAGTGTTTCCCTTCTCGAGACTTGAAAGATTATGAA
1561  ------------+---------+---------+---------+---------+---------+  1620
      CTCTCAACCCAAGAATGACGTGCTGTCACAAAGGGAAGAGCTCTGAACTTTCTAATACTT
521   E  S  W  V  L  T  A  R  Q  C  F  P  S  R  D  L  K  D  Y  E   540

GCTTGGCTTGGAATTCATGATGTCCACGGAAGAGGAGATGAGAAATGCAAACAGGTTCTC
1621  ------------+---------+---------+---------+---------+---------+  1680
      CGAACCGAACCTTAAGTACTACAGGTGCCTTCTCCTCTACTCTTTACGTTTGTCCAAGAG
541   A  W  L  G  I  H  D  V  H  G  R  G  D  E  K  C  K  Q  V  L   560

AATGTTTCCCAGCTGGTATATGGCCCTGAAGGATCAGATCTGGTTTTAATGAAGCTTGCC
1681  ------------+---------+---------+---------+---------+---------+  1740
      TTACAAAGGGTCGACCATATACCGGGACTTCCTAGTCTAGACCAAAATTACTTCGAACGG
561   N  V  S  Q  L  V  Y  G  P  E  G  S  D  L  V  L  M  K  L  A   580

AGGCCTGCTGTCCTGGATGATTTTGTTAGTACGATTGATTTACCTAATTATGGATGCACA
1741  ------------+---------+---------+---------+---------+---------+  1800
      TCCGGACGACAGGACCTACTAAAACAATCATGCTAACTAAATGGATTAATACCTACGTGT
581   R  P  A  V  L  D  D  F  V  S  T  I  D  L  P  N  Y  G  C  T   600
```

FIG.1a-3

```
     ATTCCTGAAAAGACCAGTTGCAGTGTTTATGGCTGGGGCTACACTGGATTGATCAACTAT
1801 ------------+---------+---------+---------+---------+---------+ 1860
     TAAGGACTTTTCTGGTCAACGTCACAAATACCGACCCCGATGTGACCTAACTAGTTGATA
 601  I  P  E  K  T  S  C  S  V  Y  G  W  G  Y  T  G  L  I  N  Y   620
     GATGGCCTATTACGAGTGGCACATCTCTATATAATGGGAAATGAGAAATGCAGCCAGCAT
1861 ------------+---------+---------+---------+---------+---------+ 1920
     CTACCGGATAATGCTCACCGTGTAGAGATATATTACCCTTTACTCTTTACGTCGGTCGTA
 621  D  G  L  L  R  V  A  H  L  Y  I  M  G  N  E  K  C  S  Q  H   640
     CATCGAGGGAAGGTGACTCTGAATGAGTCTGAAATATGTGCTGGGGCTGAAAAGATTGGA
1921 ------------+---------+---------+---------+---------+---------+ 1980
     GTAGCTCCCTTCCACTGAGACTTACTCAGACTTTATACACGACCCCGACTTTTCTAACCT
 641  H  R  G  K  V  T  L  N  E  S  E  I  C  A  G  A  E  K  I  G   660
     TCAGGACCATGTGAGGGGGATTATGGTGGCCCACTTGTTTGTGAGCAACATAAAATGAGA
1981 ------------+---------+---------+---------+---------+---------+ 2040
     AGTCCTGGTACACTCCCCCTAATACCACCGGGTGAACAAACACTCGTTGTATTTTACTCT
 661  S  G  P  C  E  G  D  Y  G  G  P  L  V  C  E  Q  H  K  M  R   680
     ATGGTTCTTGGTGTCATTGTTCCTGGTCGTGGATGTGCCATTCCAAATCGTCCTGGTATT
2041 ------------+---------+---------+---------+---------+---------+ 2100
     TACCAAGAACCACAGTAACAAGGACCAGCACCTACACGGTAAGGTTTAGCAGGACCATAA
 681  M  V  L  G  V  I  V  P  G  R  G  C  A  I  P  N  R  P  G  I   700
     TTTGTCCGAGTAGCATATTATGCAAAATGGATACACAAAATTATTTTAACATATAAGGTA
2101 ------------+---------+---------+---------+---------+---------+ 2160
     AAACAGGCTCATCGTATAATACGTTTTACCTATGTGTTTTAATAAAATTGTATATTCCAT
 701  F  V  R  V  A  Y  Y  A  K  W  I  H  K  I  I  L  T  Y  K  V   720
     CCACAGTCATAG
2161 ---------+-- 2172
     GGTGTCAGTATC
 721  P  Q  S  *    723
```

FIG.1a-4

```
      ATGGGGTGGCTCCCACTCCTGCTGCTTCTGACTCAATGCTTAGGGGTCCCTGGGCAGCGC
  1   ----------+---------+---------+---------+---------+---------+   60
      TACCCCACCGAGGGTGAGGACGACGAAGACTGAGTTACGAATCCCCAGGGACCCGTCGCG
  1   M  G  W  L  P  L  L  L  L  L  T  Q  C  L  G  V  P  G  Q  R    20

TCGCCATTGAATGACTTCCAAGTGCTCCGGGGCACRGAGCTACAGCACCTGCTACATGCG
 61   ----------+---------+---------+---------+---------+---------+  120
      AGCGGTAACTTACTGAAGGTTCACGAGGCCCCGTGTCTCGATGTCGTGGACGATGTACGC
 21   S  P  L  N  D  F  Q  V  L  R  G  T  E  L  Q  H  L  L  H  A    40

GTGGTGCCCGGGCCTTGGCAGGAGGATGTGGCAGATGCTGAAGAGTGTGCTGGTCGCTGT
121   ----------+---------+---------+---------+---------+---------+  180
      CACCACGGGCCCGGAACCGTCCTCCTACACCGTCTACGACTTCTCACACGACCAGCGACA
 41   V  V  P  G  P  W  Q  E  D  V  A  D  A  E  E  C  A  G  R  C    60

GGGCCCTTAATGGACTGCCGGGCCTTCCACTACAACGTGAGCAGCCATGGTTGCCAACTG
181   ----------+---------+---------+---------+---------+---------+  240
      CCCGGGAATTACCTGACGGCCCGGAAGGTGATGTTGCACTCGTCGGTACCAACGGTTGAC
 61   G  P  L  M  D  C  R  A  F  H  Y  N  V  S  S  H  G  C  Q  L    80

CTGCCATGGACTCAACACTCGCCCCACACGAGGCTGCGGCGTTCTGGGCGCTGTGACCTC
241   ----------+---------+---------+---------+---------+---------+  300
      GACGGTACCTGAGTTGTGAGCGGGGTGTGCTCCGACGCCGCAAGACCCGCGACACTGGAG
 81   L  P  W  T  Q  H  S  P  H  T  R  L  R  R  S  G  R  C  D  L   100

TTCCAGAAGAAAGACTACGTACGGACCTGCATCATGAACAATGGGGTTGGGTACCGGGGC
301   ----------+---------+---------+---------+---------+---------+  360
      AAGGTCTTCTTTCTGATGCATGCCTGGACGTAGTACTTGTTACCCCAACCCATGGCCCCG
101   F  Q  K  K  D  Y  V  R  T  C  I  M  N  N  G  V  G  Y  R  G   120

ACCATGGCCACGACCGTGGGTGGCCTGCCCTGCCAGGCTTGGAGCCACAAGTTCCCGAAT
361   ----------+---------+---------+---------+---------+---------+  420
      TGGTACCGGTGCTGGCACCCACCGGACGGGACGGTCCGAACCTCGGTGTTCAAGGGCTTA
121   T  M  A  T  T  V  G  G  L  P  C  Q  A  W  S  H  K  F  P  N   140

GATCACAAGTACACGCCCACTCTCCGGAATGGCCTGGAAGAGAACTTCTGCCGTAACCCT
421   ----------+---------+---------+---------+---------+---------+  480
      CTAGTGTTCATGTGCGGGTGAGAGGCCTTACCGGACCTTCTCTTGAAGACGGCATTGGGA
141   D  H  K  Y  T  P  T  L  R  N  G  L  E  E  N  F  C  R  N  P   160
```

FIG.1b-1

```
     GATGGCGACCCCGGAGGTCCTTGGTGCTACACAACAGACCCTGCTGTGCGCTTCCAGAGC
481  ---------+---------+---------+---------+---------+---------+  540
     CTACCGCTGGGGCCTCCAGGAACCACGATGTGTTGTCTGGGACGACACGCGAAGGTCTCG
161  D   G   D   P   G   G   P   W   C   Y   T   T   D   P   A   V   R   F   Q   S   180

TGCGGCATCAAATCCTGCCGGGAGGCCGCGTGTGTCTGGTGCAATGGCGAGGAATACCGC
531  ---------+---------+---------+---------+---------+---------+  600
     ACGCCGTAGTTTAGGACGGCCCTCCGGCGCACACAGACCACGTTACCGCTCCTTATGGCG
181  C   G   I   K   S   C   R   E   A   A   C   V   W   C   N   G   E   E   Y   R   200

GGCGCGGTAGACCGCACGGAGTCAGGGCGCGAGTGCCAGCGCTGGGATCTTCAGCACCCG
601  ---------+---------+---------+---------+---------+---------+  660
     CCGCGCCATCTGGCGTGCCTCAGTCCCGCGCTCACGGTCGCGACCCTAGAAGTCGTGGGC
201  G   A   V   D   R   T   E   S   G   R   E   C   Q   R   W   D   L   Q   H   P   220

CACCAGCACCCCTTCGAGCCGGGCAAGTTCCTCGACCAAGGTCTGGACGACAACTATTGC
661  ---------+---------+---------+---------+---------+---------+  720
     GTGGTCGTGGGGAAGCTCGGCCCGTTCAAGGAGCTGGTTCCAGACCTGCTGTTGATAACG
221  H   Q   H   P   F   E   P   G   K   F   L   D   Q   G   L   D   D   N   Y   C   240

CGGAATCCTGACGGCTCCGAGCGGCCATGGTGCTACACTACGGATCCGCAGATCGAGCGA
721  ---------+---------+---------+---------+---------+---------+  780
     GCCTTAGGACTGCCGAGGCTCGCCGGTACCACGATGTGATGCCTAGGCGTCTAGCTCGCT
241  R   N   P   D   G   S   E   R   P   W   C   Y   T   T   D   P   Q   I   E   R   260

GAGTTCTGTGACCTCCCCCGCTGCGGGTCCGAGGCACAGCCCCGCCAAGAGGCCACAACT
781  ---------+---------+---------+---------+---------+---------+  840
     CTCAAGACACTGGAGGGGGCGACGCCCAGGCTCCGTGTCGGGGCGGTTCTCCGGTGTTGA
261  E   F   C   D   L   P   R   C   G   S   E   A   Q   P   R   Q   E   A   T   T   280

GTCAGCTGCTTCCGCGGGAAGGGTGAGGGCTACCGGGGCACAGCCAATACCACCACTGCG
841  ---------+---------+---------+---------+---------+---------+  900
     CAGTCGACGAAGGCGCCCTTCCCACTCCCGATGGCCCCGTGTCGGTTATGGTGGTGACGC
281  V   S   C   F   R   G   K   G   E   G   Y   R   G   T   A   N   T   T   T   A   300

GGCGTACCTTGCCAGCGTTGGGACGCGCAAATCCCGCATCAGCACCGATTTACGCCAGAA
901  ---------+---------+---------+---------+---------+---------+  960
     CCGCATGGAACGGTCGCAACCCTGCGCGTTTAGGGCGTAGTCGTGGCTAAATGCGGTCTT
301  G   V   P   C   Q   R   W   D   A   Q   I   P   H   Q   H   R   F   T   P   E   320

AAATACGCGTGCAAAGACCTTCGGGAGAACTTCTGCCGGAACCCCGACGGCTCAGAGGCG
961  ---------+---------+---------+---------+---------+---------+  1020
     TTTATGCGCACGTTTCTGGAAGCCCTCTTGAAGACGGCCTTGGGGCTGCCGAGTCTCCGC
321  K   Y   A   C   K   D   L   R   E   N   F   C   R   N   P   D   G   S   E   A   340

CCCTGGTGCTTCACACTGCGGCCCGGCATGCGCGCGGCCTTTTGCTACCAGATCCGGCGT
1021 ---------+---------+---------+---------+---------+---------+  1080
     GGGACCACGAAGTGTGACGCCGGGCCGTACGCGCGCCGGAAAACGATGGTCTAGGCCGCA
341  P   W   C   F   T   L   R   P   G   M   R   A   A   F   C   Y   Q   I   R   R   360

TGTACAGACGACGTGCGGCCCCAGGACTGCTACCACGGCGCAGGGGAGCAGTACCGCGGC
1081 ---------+---------+---------+---------+---------+---------+  1140
     ACATGTCTGCTGCACGCCGGGGTCCTGACGATGGTGCCGCGTCCCCTCGTCATGGCGCCG
361  C   T   D   D   V   R   P   Q   D   C   Y   H   G   A   G   E   Q   Y   R   G   380
```

FIG.1b-2

```
          ACGGTCAGCAAGACCCGCAAGGGTGTCCAGTGCCAGCGCTGGTCCGCTGAGACGCCGCAC
1141      ---------+---------+---------+---------+---------+---------+   1200
          TGCCAGTCGTTCTGGGCGTTCCCACAGGTCACGGTCGCGACCAGGCGACTCTGCGGCGTG
381       T   V   S   K   T   R   K   G   V   Q   C   Q   R   W   S   A   E   T   P   H   400
          AAGCCGCAGTTCACGTTTACCTCCGAACCGCATGCACAACTGGAGGAGAACTTCTGCCGG
1201      ---------+---------+---------+---------+---------+---------+   1260
          TTCGGCGTCAAGTGCAAATGGAGGCTTGGCGTACGTGTTGACCTCCTCTTGAAGACGGCC
401       K   P   Q   F   T   F   T   S   E   P   H   A   Q   L   E   E   N   F   C   R   420
          AACCCAGATGGGGATAGCCATGGGCCCTGGTGCTACACGATGGACCCAAGGACCCCATTC
1261      ---------+---------+---------+---------+---------+---------+   1320
          TTGGGTCTACCCCTATCGGTACCCGGGACCACGATGTGCTACCTGGGTTCCTGGGGTAAG
421       N   P   D   G   D   S   H   G   P   W   C   Y   T   M   D   P   R   T   P   F   440
          GACTACTGTGCCCTGCGACGCTGCGCTGATGACCAGCCGCCATCAATCCTGGACCCCCCA
1321      ---------+---------+---------+---------+---------+---------+   1380
          CTGATGACACGGGACGCTGCGACGCGACTACTGGTCGGCGGTAGTTAGGACCTGGGGGGT
441       D   Y   C   A   L   R   R   C   A   D   D   Q   P   P   S   I   L   D   P   P   460
          GACCAGGTGCAGTTTGAGAAGTGTGGCAAGAGGGTGGATCGGCTGGATCAGCGGCGTTCC
1381      ---------+---------+---------+---------+---------+---------+   1440
          CTGGTCCACGTCAAACTCTTCACACCGTTCTCCCACCTAGCCGACCTAGTCGCCGCAAGG
461       D   Q   V   Q   F   E   K   C   G   K   R   V   D   R   L   D   Q   R   R   S   480
          AAGCTGCGCGTGGTTGGGGGCCATCCGGGCAACTCACCCTGGACAGTCAGCTTGCGGAAT
1441      ---------+---------+---------+---------+---------+---------+   1500
          TTCGACGCGCACCAACCCCCGGTAGGCCCGTTGAGTGGGACCTGTCAGTCGAACGCCTTA
481       K   L   R   V   V   G   G   H   P   G   N   S   P   W   T   V   S   L   R   N   500
          CGGCAGGGCCAGCATTTCTGCGGGGGGTCTCTAGTGAAGGAGCAGTGGATACTGACTGCC
1501      ---------+---------+---------+---------+---------+---------+   1560
          GCCGTCCCGGTCGTAAAGACGCCCCCCAGAGATCACTTCCTCGTCACCTATGACTGACGG
501       R   Q   G   Q   H   F   C   G   G   S   L   V   K   E   Q   W   I   L   T   A   520
          CGGCAGTGCTTCTCCTCCTGCCATATGCCTCTCACGGGCTATGAGGTATGGTTGGGCACC
1561      ---------+---------+---------+---------+---------+---------+   1620
          GCCGTCACGAAGAGGAGGACGGTATACGGAGAGTGCCCGATACTCCATACCAACCCGTGG
521       R   Q   C   F   S   S   C   H   M   P   L   T   G   Y   E   V   W   L   G   T   540
          CTGTTCCAGAACCCACAGCATGGAGAGCCAAGCCTACAGCGGGTCCCAGTAGCCAAGATG
1621      ---------+---------+---------+---------+---------+---------+   1680
          GACAAGGTCTTGGGTGTCGTACCTCTCGGTTCGGATGTCGCCCAGGGTCATCGGTTCTAC
541       L   F   Q   N   P   Q   H   G   E   P   S   L   Q   R   V   P   V   A   K   M   560
          GTGTGTGGGCCCTCAGGCTCCCAGCTTGTCCTGCTCAAGCTGGAGAGATCTGTGACCCTG
1681      ---------+---------+---------+---------+---------+---------+   1740
          CACACACCCGGGAGTCCGAGGGTCGAACAGGACGAGTTCGACCTCTCTAGACACTGGGAC
561       V   C   G   P   S   G   S   Q   L   V   L   L   K   L   E   R   S   V   T   L   580
          AACCAGCGTGTGGCCCTGATCTGCCTGCCCCCTGAATGGTATGTGGTGCCTCCAGGGACC
1741      ---------+---------+---------+---------+---------+---------+   1800
          TTGGTCGCACACCGGGACTAGACGGACGGGGGACTTACCATACACCACGGAGGTCCCTGG
581       N   Q   R   V   A   L   I   C   L   P   P   E   W   Y   V   V   P   P   G   T   600
```

FIG.1b-3

```
           AAGTGTGAGATTGCAGGCTGGGGTGAGACCAAAGGTACGGGTAATGACACAGTCCTAAAT
1801       ---------+---------+---------+---------+---------+---------+  1860
           TTCACACTCTAACGTCCGACCCCACTCTGGTTTCCATGCCCATTACTGTGTCAGGATTTA
 601    K  C  E  I  A  G  W  G  E  T  K  G  T  G  N  D  T  V  L  N    620
           GTGGCCTTTCTGAATGTTATCTCCAACCAGGAGTGTAACATCAAGCACCGAGGACGTGTG
1861       ---------+---------+---------+---------+---------+---------+  1920
           CACCGGAAAGACTTACAATAGAGGTTGGTCCTCACATTGTAGTTCGTGGCTCCTGCACAC
 621    V  A  F  L  N  V  I  S  N  Q  E  C  N  I  K  H  R  G  R  V    640
           CGGGAGAGTGAGATGTGCACTGAGGGACTGTTGGCCCCTGTGGGGGCCTGTGAGGGTGAC
1921       ---------+---------+---------+---------+---------+---------+  1980
           GCCCTCTCACTCTACACGTGACTCCCTGACAACCGGGGACACCCCCGGACACTCCCACTG
 641    R  E  S  E  M  C  T  E  G  L  L  A  P  V  G  A  C  E  G  D    660
           TACGGGGGCCCACTTGCCTGCTTTACCCACAACTGCTGGGTCCTGGAAGGAATTATAATC
1981       ---------+---------+---------+---------+---------+---------+  2040
           ATGCCCCCGGGTGAACGGACGAAATGGGTGTTGACGACCCAGGACCTTCCTTAATATTAG
 661    Y  G  G  P  L  A  C  F  T  H  N  C  W  V  L  E  G  I  I  I    680
           CCCAACCGAGTATGCGCAAGGTCCCGCTGGCCAGCTGTCTTCACGCGTGTCTCTGTGTTT
2041       ---------+---------+---------+---------+---------+---------+  2100
           GGGTTGGCTCATACGCGTTCCAGGGCGACCGGTCGACAGAAGTGCGCACAGAGACACAAA
 681    P  N  R  V  C  A  R  S  R  W  P  A  V  F  T  R  V  S  V  F    700
           GTGGACTGGATTCACAAGGTCATGAGACTGGGTTAG
2101       ---------+---------+---------+------  2136
           CACCTGACCTAAGTGTTCCAGTACTCTGACCCAATC
 701    V  D  W  I  H  K  V  M  R  L  G  *                              711
```

FIG.1b-4

```
    GAATTCCACCATGGGGTGGCTCCCACTCCTGCTGCTTCTGACTCAATGCTTAGGGGTCCC
  1 ---------+---------+---------+---------+---------+---------+  60
    CTTAAGGTGGTACCCCACCGAGGGTGAGGACGACGAAGACTGAGTTACGAATCCCCAGGG
  1         M  G  W  L  P  L  L  L  L  L  T  Q  C  L  G  V  P    17

TGGGCAGCGCTCGCCATTGAATGACTTCCAAGTGCTCCGGGGCACAGAGCTACAGCACCT
 61 ---------+---------+---------+---------+---------+---------+ 120
    ACCCGTCGCGAGCGGTAACTTACTGAAGGTTCACGAGGCCCCGTGTCTCGATGTCGTGGA
 18  G  Q  R  S  P  L  N  D  F  Q  V  L  R  G  T  E  L  Q  H  L   37

GCTACATGCGGTGGTGCCCGGGCCTTGGCAGGAGGATGTGGCAGATGCTGAAGAGTGTGC
121 ---------+---------+---------+---------+---------+---------+ 180
    CGATGTACGCCACCACGGGCCCGGAACCGTCCTCCTACACCGTCTACGACTTCTCACACG
 38  L  H  A  V  V  P  G  P  W  Q  E  D  V  A  D  A  E  E  C  A   57

TGGTCGCTGTGGGCCCTTAATGGACTGCCGGGCCTTCCACTACAACGTGAGCAGCCATGG
181 ---------+---------+---------+---------+---------+---------+ 240
    ACCAGCGACACCCGGGAATTACCTGACGGCCCGGAAGGTGATGTTGCACTCGTCGGTACC
 58  G  R  C  G  P  L  M  D  C  R  A  F  H  Y  N  V  S  S  H  G   77

TTGCCAACTGCTGCCATGGACTCAACACTCGCCCCACACGAGGCTGCGGCGTTCTGGGCG
241 ---------+---------+---------+---------+---------+---------+ 300
    AACGGTTGACGACGGTACCTGAGTTGTGAGCGGGGTGTGCTCCGACGCCGCAAGACCCGC
 78  C  Q  L  L  P  W  T  Q  H  S  P  H  T  R  L  R  R  S  G  R   97

CTGTGACCTCTTCCAGAAGAAAGACTACGTACGGACCTGCATCATGAACAATGGGGTTGG
301 ---------+---------+---------+---------+---------+---------+ 360
    GACACTGGAGAAGGTCTTCTTTCTGATGCATGCCTGGACGTAGTACTTGTTACCCCAACC
 98  C  D  L  F  Q  K  K  D  Y  V  R  T  C  I  M  N  N  G  V  G  117

GTACCGGGGCACCATGGCCACGACCGTGGGTGGCCTGCCCTGCCAGGCTTGGAGCCACAA
361 ---------+---------+---------+---------+---------+---------+ 420
    CATGGCCCCGTGGTACCGGTGCTGGCACCCACCGGACGGGACGGTCCGAACCTCGGTGTT
118  Y  R  G  T  M  A  T  T  V  G  G  L  P  C  Q  A  W  S  H  K  137

GTTCCCGAATGATCACAAGTACACGCCCACTCTCCGGAATGGCCTGGAAGAGAACTTCTG
421 ---------+---------+---------+---------+---------+---------+ 480
    CAAGGGCTTACTAGTGTTCATGTGCGGGTGAGAGGCCTTACCGGACCTTCTCTTGAAGAC
138  F  P  N  D  H  K  Y  T  P  T  L  R  N  G  L  E  E  N  F  C  157

CCGTAACCCTGATGGCGACCCCGGAGGTCCTTGGTGCTACACAACAGACCCTGCTGTGCG
481 ---------+---------+---------+---------+---------+---------+ 540
    GGCATTGGGACTACCGCTGGGGCCTCCAGGAACCACGATGTGTTGTCTGGGACGACACGC
159  R  N  P  D  G  D  P  G  G  P  W  C  Y  T  T  D  P  A  V  R  177
```

FIG.2b-1

```
     CTTCCAGAGCTGCGGCATCAAATCCTGCCGGGAGGCCGCGTGTGTCTGGTGCAATGGCGA
541  ---------+---------+---------+---------+---------+---------+  600
     GAAGGTCTCGACGCCGTAGTTTAGGACGGCCCTCCGGCGCACACAGACCACGTTACCGCT
178   F  Q  S  C  G  I  K  S  C  R  E  A  A  C  V  W  C  N  G  E   197

GGAATACCGCGGCGCGGTAGACCGCACGGAGTCAGGGCGCGAGTGCCAGCGCTGGGATCT
601  ---------+---------+---------+---------+---------+---------+  660
     CCTTATGGCGCCGCGCCATCTGGCGTGCCTCAGTCCCGCGCTCACGGTCGCGACCCTAGA
198   E  Y  R  G  A  V  D  R  T  E  S  G  R  E  C  Q  R  W  D  L   217

TCAGCACCCGCACCAGCACCCCTTCGAGCCGGGCAAGTTCCTCGACCAAGGTCTGGACGA
661  ---------+---------+---------+---------+---------+---------+  720
     AGTCGTGGGCGTGGTCGTGGGGAAGCTCGGCCCGTTCAAGGAGCTGGTTCCAGACCTGCT
218   Q  H  P  H  Q  H  P  F  E  P  G  K  F  L  D  Q  G  L  D  D   237

CAACTATTGCCGGAATCCTGACGGCTCCGAGCGGCCATGGTGCTACACTACGGATCCGCA
721  ---------+---------+---------+---------+---------+---------+  780
     GTTGATAACGGCCTTAGGACTGCCGAGGCTCGCCGGTACCACGATGTGATGCCTAGGCGT
238   N  Y  C  R  N  P  D  G  S  E  R  P  W  C  Y  T  T  D  P  Q   257

GATCGAGCGAGAGTTCTGTGACCTCCCCCGCTGCGGGTCCGAGGCACAGCCCCGCCTCGA
781  ---------+---------+---------+---------+---------+---------+  840
     CTAGCTCGCTCTCAAGACACTGGAGGGGGCGACGCCCAGGCTCCGTGTCGGGGCGGAGCT
258   I  E  R  E  F  C  D  L  P  R  C  G  S  E  A  Q  P  R  L  E   277

GGGCGGTGGCGGTTCTGGTGGCGGTGGCTCCGGCGGTGGCGGTTCTCTAGAGGGACAAAG
841  ---------+---------+---------+---------+---------+---------+  900
     CCCGCCACCGCCAAGACCACCGCCACCGAGGCCGCCACCGCCAAGAGATCTCCCTGTTTC
278   G  G  G  G  S  G  G  G  G  S  G  G  G  G  S  L  E  G  Q  R   297

GAAAAGAAGAAATACAATTCATGAATTCAAAAAATCAGCAAAGACTACCCTAATCAAAT
901  ---------+---------+---------+---------+---------+---------+  960
     CTTTTCTTCTTTATGTTAAGTACTTAAGTTTTTTAGTCGTTTCTGATGGGATTAGTTTTA
298   K  R  R  N  T  I  H  E  F  K  K  S  A  K  T  T  L  I  K  I   317

AGATCCAGCACTGAAGATAAAAACCAAAAAAGTGAATACTGCAGACCAATGTGCTAATAG
961  ---------+---------+---------+---------+---------+---------+  1020
     TCTAGGTCGTGACTTCTATTTTTGGTTTTTTCACTTATGACGTCTGGTTACACGATTATC
318   D  P  A  L  K  I  K  T  K  K  V  N  T  A  D  Q  C  A  N  R   337

ATGTACTAGGAATAAAGGACTTCCATTCACTTGCAAGGCTTTTGTTTTTGATAAAGCAAG
1021 ---------+---------+---------+---------+---------+---------+  1080
     TACATGATCCTTATTTCCTGAAGGTAAGTGAACGTTCCGAAAACAAAAACTATTTCGTTC
338   C  T  R  N  K  G  L  P  F  T  C  K  A  F  V  F  D  K  A  R   357

AAAACAATGCCTCTGGTTCCCCTTCAATAGCATGTCAAGTGGAGTGAAAAAAGAATTTGG
1081 ---------+---------+---------+---------+---------+---------+  1140
     TTTTGTTACGGAGACCAAGGGGAAGTTATCGTACAGTTCACCTCACTTTTTTCTTAAACC
358   K  Q  C  L  W  F  P  F  N  S  M  S  S  G  V  K  K  E  F  G   377

CCATGAATTTGACCTCTATGAAAACAAAGACTACATTAGAAACTGCATCATTGGTAAAGG
1141 ---------+---------+---------+---------+---------+---------+  1200
     GGTACTTAAACTGGAGATACTTTTGTTTCTGATGTAATCTTTGACGTAGTAACCATTTCC
378   H  E  F  D  L  Y  E  N  H  D  Y  I  R  N  C  I  I  G  K  G   397
```

FIG.2b-2

```
     ACGCAGCTACAAGGGAACAGTATCTATCACTAAGAGTGGCATCAAATGTCAGCCCTGGAG
1201 ----------+---------+---------+---------+---------+---------+ 1260
     TGCGTCGATGTTCCCTTGTCATAGATAGTGATTCTCACCGTAGTTTACAGTCGGGACCTC
398   R  S  Y  K  G  T  V  S  I  T  K  S  G  I  K  C  Q  P  W  S  417

TTCCATGATACCACACGAACACAGCTATCGGGGTAAAGACCTACAGGAAAACTACTGTCG
1261 ----------+---------+---------+---------+---------+---------+ 1320
     AAGGTACTATGGTGTGCTTGTGTCGATAGCCCCATTTCTGGATGTCCTTTTGATGACAGC
418   S  M  I  P  H  E  H  S  Y  R  G  K  D  L  Q  E  N  Y  C  R  437

AAATCCTCGAGGGGAAGAAGGGGGACCCTGGTGTTTCACAAGCAATCCAGAGGTACGCTA
1321 ----------+---------+---------+---------+---------+---------+ 1380
     TTTAGGAGCTCCCCTTCTTCCCCCTGGGACCACAAAGTGTTCGTTAGGTCTCCATGCGAT
438   N  P  R  G  E  E  G  G  P  W  C  F  T  S  N  P  E  V  R  Y  457

CGAAGTCTGTGACATTCCTCAGTGTTCAGAAGTTGAATGCATGACCTGCAATGGGGAGAG
1381 ----------+---------+---------+---------+---------+---------+ 1440
     GCTTCAGACACTGTAAGGAGTCACAAGTCTTCAACTTACGTACTGGACGTTACCCCTCTC
458   E  V  C  D  I  P  Q  C  S  E  V  E  C  M  T  C  N  G  E  S  477

TTATCGAGGTCTCATGGATCATACAGAATCAGGCAAGATTTGTCAGCGCTGGGATCATCA
1441 ----------+---------+---------+---------+---------+---------+ 1500
     AATAGCTCCAGAGTACCTAGTATGTCTTAGTCCGTTCTAAACAGTCGCGACCCTAGTAGT
478   Y  R  G  L  M  D  H  T  E  S  G  K  I  C  Q  R  W  D  H  Q  497

GACACCACACCGGCACAAATTCTTGCCTGAAAGATATCCCGACAAGGGCTTTGATGATAA
1501 ----------+---------+---------+---------+---------+---------+ 1560
     CTGTGGTGTGGCCGTGTTTAAGAACGGACTTTCTATAGGGCTGTTCCCGAAACTACTATT
498   T  P  H  R  H  K  F  L  P  E  R  Y  P  D  K  G  F  D  D  N  517

TTATTGCCGCAATCCCGATGGCCAGCCGAGGCCATGGTGCTATACTCTTGACCCTCACAC
1561 ----------+---------+---------+---------+---------+---------+ 1620
     AATAACGGCGTTAGGGCTACCGGTCGGCTCCGGTACCACGATATGAGAACTGGGAGTGTG
518   Y  C  R  N  P  D  G  Q  P  R  P  W  C  Y  T  L  D  P  H  T  537

CCGCTGGGAGTACTGTGCAATTAAAAACATGCGCTGACAAAGCTGACGACGACGACAAACA
1621 ----------+---------+---------+---------+---------+---------+ 1680
     GGCGACCCTCATGACACGTTAATTTTGTACGCGACTGTTTCGACTGCTGCTGCTGTTTGT
538   R  W  E  Y  C  A  I  K  T  C  A  D  K  A  D  D  D  D  K  H  557

CCACCACCACCACCACCACTAGGGTCGAC
1681 ----------+---------+-------- 1709
     GGTGGTGGTGGTGGTGGTGATCCCAGCTG
558   H  H  H  H  H  H  *           563
```

FIG.2b-3

```
     GGATCCGCCAGCCCGTCCAGCAGCACCATGTGGGTGACCAAACTCCTGCCAGCCCTGCTG
1    ---------+---------+---------+---------+---------+---------+  60
     CCTAGGCGGTCGGGCAGGTCGTCGTGGTACACCCACTGGTTTGAGGACGGTCGGGACGAC
1                                  M  W  V  T  K  L  L  P  A  L  L    11
     CTGCAGCATGTCCTCCTGCATCTCCTCCTGCTCCCCATCGCCATCCCCTATGCAGAGGGA
61   ---------+---------+---------+---------+---------+---------+  120
     GACGTCGTACAGGAGGACGTAGAGGAGGACGAGGGGTAGCGGTAGGGGATACGTCTCCCT
12    L  Q  H  V  L  L  H  L  L  L  P  I  A  I  P  Y  A  E  G    31
     CAAAGGAAAAGAAGAAATACAATTCATGAATTCAAAAAATCAGCAAAGACTACCCTAATC
121  ---------+---------+---------+---------+---------+---------+  180
     GTTTCCTTTTCTTCTTTATGTTAAGTACTTAAGTTTTTTAGTCGTTTCTGATGGGATTAG
32    Q  R  K  R  R  N  T  I  H  E  F  K  K  S  A  K  T  T  L  I    51
     AAAATAGATCCAGCACTGAAGATAAAAACCAAAAAAGTGAATACTGCAGACCAATGTGCT
181  ---------+---------+---------+---------+---------+---------+  240
     TTTTATCTAGGTCGTGACTTCTATTTTTGGTTTTTTCACTTATGACGTCTGGTTACACGA
52    K  I  D  P  A  L  K  I  K  T  K  K  V  N  T  A  D  Q  C  A    71
     AATAGATGTACTAGGAATAAAGGACTTCCATTCACTTGCAAGGCTTTTGTTTTTGATAAA
241  ---------+---------+---------+---------+---------+---------+  300
     TTATCTACATGATCCTTATTTCCTGAAGGTAAGTGAACGTTCCGAAAACAAAAACTATTT
72    N  R  C  T  R  N  K  G  L  P  F  T  C  K  A  F  V  F  D  K    91
     GCAAGAAAACAATGCCTCTGGTTCCCCTTCAATAGCATGTCAAGTGGAGTGAAAAAAGAA
301  ---------+---------+---------+---------+---------+---------+  360
     CGTTCTTTTGTTACGGAGACCAAGGGGAAGTTATCGTACAGTTCACCTCACTTTTTTCTT
92    A  R  K  Q  C  L  W  F  P  F  N  S  M  S  S  G  V  K  K  E   111
     TTTGGCCATGAATTTGACCTCTATGAAAACAAAGACTACATTAGAAACTGCATCATTGGT
361  ---------+---------+---------+---------+---------+---------+  420
     AAACCGGTACTTAAACTGGAGATACTTTTGTTTCTGATGTAATCTTTGACGTAGTAACCA
112   F  G  H  E  F  D  L  Y  E  N  K  D  Y  I  R  N  C  I  I  G   131
     AAAGGACGCAGCTACAAGGGAACAGTATCTATCACTAAGAGTGGCATCAAATGTCAGCCC
421  ---------+---------+---------+---------+---------+---------+  480
     TTTCCTGCGTCGATGTTCCCTTGTCATAGATAGTGATTCTCACCGTAGTTTACAGTCGGG
132   K  G  R  S  Y  K  G  T  V  S  I  T  K  S  G  I  K  C  Q  P   151
     TGGAGTTCCATGATACCACACGAACACAGCTATCGGGGTAAAGACCTACAGGAAAACTAC
481  ---------+---------+---------+---------+---------+---------+  540
     ACCTCAAGGTACTATGGTGTGCTTGTGTCGATAGCCCCATTTCTGGATGTCCTTTTGATG
152   W  S  S  M  I  P  H  E  H  S  Y  R  G  K  D  L  Q  E  N  Y   171
```

FIG.3b-1

```
     TGTCGAAATCCTCGAGGGGAAGAAGGGGGACCCTGGTGTTTCACAAGCAATCCAGAGGTA
541  ---------+---------+---------+---------+---------+---------+  600
     ACAGCTTTAGGAGCTCCCCTTCTTCCCCCTGGGACCACAAAGTGTTCGTTAGGTCTCCAT
172   C  R  N  P  R  G  E  E  G  G  P  W  C  F  T  S  N  P  E  V   191
     CGCTACGAAGTCTGTGACATTCCTCAGTGTTCAGAAGTTGAATGCATGACCTGCAATGGG
601  ---------+---------+---------+---------+---------+---------+  660
     GCGATGCTTCAGACACTGTAAGGAGTCACAAGTCTTCAACTTACGTACTGGACGTTACCC
192   R  Y  E  V  C  D  I  P  Q  C  S  E  V  E  C  M  T  C  N  G   211
     GAGAGTTATCGAGGTCTCATGGATCATACAGAATCAGGGAAGATTTGTCAGCGCTGGGAT
661  ---------+---------+---------+---------+---------+---------+  720
     CTCTCAATAGCTCCAGAGTACCTAGTATGTCTTAGTCCGTTCTAAACAGTCGCGACCCTA
212   E  S  Y  R  G  L  M  D  H  T  E  S  G  K  I  C  Q  R  W  D   231
     CATCAGACACCACACCGGCACAAATTCTTGCCTGAAAGATATCCCGACAAGGGCTTTGAT
721  ---------+---------+---------+---------+---------+---------+  780
     GTAGTCTGTGGTGTGGCCGTGTTTAAGAACGGACTTTCTATAGGGCTGTTCCCGAAACTA
232   H  Q  T  P  H  R  H  K  F  L  P  E  R  Y  P  D  K  G  F  D   251
     GATAATTATTGCCGCAATCCCGATGGCCAGCCGAGGCCATGGTGCTATACTCTTGACCCT
781  ---------+---------+---------+---------+---------+---------+  840
     CTATTAATAACGGCGTTAGGGCTACCGGTCGGCTCCGGTACCACGATATGAGAACTGGGA
252   D  N  Y  C  R  N  P  D  G  Q  P  R  P  W  C  Y  T  L  D  P   271
     CACACCCGCTGGGAGTACTGTGCAATTAAAACATGCGCTGACAAAGCTTCGGGCGGTGGC
841  ---------+---------+---------+---------+---------+---------+  900
     GTGTGGGCGACCCTCATGACACGTTAATTTTGTACGCGACTGTTTCGAAGCCCGCCACCG
272   H  T  R  W  E  Y  C  A  I  K  T  C  A  D  K  A  S  G  G  G   291
     GGTTCTGGTGGCGGTGGCTCCGGCGGTGGCGGTTCTCTAGAGGGACAAAGGAAAAGAAGA
901  ---------+---------+---------+---------+---------+---------+  960
     CCAAGACCACCGCCACCGAGGCCGCCACCGCCAAGAGATCTCCCTGTTTCCTTTTCTTCT
292   G  S  G  G  G  G  S  G  G  G  G  S  L  E  G  Q  R  K  R  R   311
     AATACAATTCATGAATTCAAAAAAATCAGCAAAGACTACCCTAATCAAAATAGATCCAGCA
961  ---------+---------+---------+---------+---------+---------+  1020
     TTATGTTAAGTACTTAAGTTTTTTTAGTCGTTTCTGATGGGATTAGTTTTATCTAGGTCGT
312   N  T  I  H  E  F  K  K  S  A  K  T  T  L  I  K  I  D  P  A   331
     CTGAAGATAAAAACCAAAAAAGTGAATACTGCAGACCAATGTGCTAATAGATGTACTAGG
1021 ---------+---------+---------+---------+---------+---------+  1080
     GACTTCTATTTTTGGTTTTTTCACTTATGACGTCTGGTTACACGATTATCTACATGATCC
332   L  K  I  K  T  K  K  V  N  T  A  D  Q  C  A  N  R  C  T  R   351
     AATAAAGGACTTCCATTCACTTGCAAGGCTTTTGTTTTTGATAAAGCAAGAAAACAATGC
1081 ---------+---------+---------+---------+---------+---------+  1140
     TTATTTCCTGAAGGTAAGTGAACGTTCCGAAAACAAAAACTATTTCGTTCTTTTGTTACG
352   N  K  G  L  P  F  T  C  K  A  F  V  F  D  K  A  R  K  Q  C   371
     CTCTGGTTCCCCTTCAATAGCATGTCAAGTGGAGTGAAAAAAGAATTTGGCCATGAATTT
1141 ---------+---------+---------+---------+---------+---------+  1200
     GAGACCAAGGGGAAGTTATCGTACAGTTCACCTCACTTTTTTCTTAAACCGGTACTTAAA
372   L  W  F  P  F  N  S  M  S  S  G  V  K  K  E  F  G  H  E  F   391
```

FIG.3b-2

```
     GACCTCTATGAAAACAAAGACTACATTAGAAACTGCATCATTGGTAAAGGACGCAGCTAC
1201 ----------+---------+---------+---------+---------+---------+ 1260
     CTGGAGATACTTTTGTTTCTGATGTAATCTTTGACGTAGTAACCATTTCCTGCGTCGATG
392  D  L  Y  E  N  K  D  Y  I  R  N  C  I  I  G  K  G  R  S  Y  411
     AAGGGAACAGTATCTATCACTAAGAGTGGCATCAAATGTCAGCCCTGGAGTTCCATGATA
1261 ----------+---------+---------+---------+---------+---------+ 1320
     TTCCCTTGTCATAGATAGTGATTCTCACCGTAGTTTACAGTCGGGACCTCAAGGTACTAT
412  K  G  T  V  S  I  T  K  S  G  I  K  C  Q  P  W  S  S  M  I  431
     CCACACGAACACAGCTATCGGGGTAAAGACCTACAGGAAAACTACTGTCGAAATCCTCGA
1321 ----------+---------+---------+---------+---------+---------+ 1380
     GGTGTGCTTGTGTCGATAGCCCCATTTCTGGATGTCCTTTTGATGACAGCTTTAGGAGCT
432  P  H  E  S  Y  R  G  K  D  L  Q  E  N  Y  C  R  N  P  R  451
     GGGGAAGAAGGGGGACCCTGGTGTTTCACAAGCAATCCAGAGGTACGCTACGAAGTCTGT
1381 ----------+---------+---------+---------+---------+---------+ 1440
     CCCCTTCTTCCCCCTGGGACCACAAAGTGTTCGTTAGGTCTCCATGCGATGCTTCAGACA
452  G  E  E  G  P  W  C  F  T  S  N  P  E  V  R  Y  E  V  C  471
     GACATTCCTCAGTGTTCAGAAGTTGAATGCATGACCTGCAATGGGGAGAGTTATCGAGGT
1441 ----------+---------+---------+---------+---------+---------+ 1500
     CTGTAAGGAGTCACAAGTCTTCAACTTACGTACTGGACGTTACCCCTCTCAATAGCTCCA
472  D  I  P  Q  C  S  E  V  E  C  M  T  C  N  G  E  S  Y  R  G  491
     CTCATGGATCATACAGAATCAGGCAAGATTTGTCAGCGCTGGGATCATCAGACACCACAC
1501 ----------+---------+---------+---------+---------+---------+ 1560
     GAGTACCTAGTATGTCTTAGTCCGTTCTAAACAGTCGCGACCCTAGTAGTCTGTGGTGTG
492  L  M  D  H  T  E  S  G  K  I  C  Q  R  W  D  H  Q  T  P  H  511
     CGGCACAAATTCTTGCCTGAAAGATATCCCGACAAGGGCTTTGATGATAATTATTGCCGC
1561 ----------+---------+---------+---------+---------+---------+ 1620
     GCCGTGTTTAAGAACGGACTTTCTATAGGGCTGTTCCCGAAACTACTATTAATAACGGCG
512  R  H  K  F  L  P  E  R  Y  P  D  K  G  F  D  D  N  Y  C  R  531
     AATCCCGATGGCCAGCCGAGGCCATGGTGCTATACTCTTGACCCTCACACCCGCTGGGAG
1621 ----------+---------+---------+---------+---------+---------+ 1680
     TTAGGGCTACCGGTCGGCTCCGGTACCACGATATGAGAACTGGGAGTGTGGGCGACCCTC
532  N  P  D  G  Q  P  R  P  W  C  Y  T  L  D  P  H  T  R  W  E  551
     TACTGTGCAATTAAAACATGCGCTGACAAAGCTGACGACGACGACAAACACCACCACCAC
1681 ----------+---------+---------+---------+---------+---------+ 1740
     ATGACACGTTAATTTTGTACGCGACTGTTTCGACTGCTGCTGCTGTTTGTGGTGGTGGTG
552  Y  C  A  I  K  T  C  A  D  K  A  D  D  D  D  K  H  H  H  H  571
     CACCACCACTAGGGTCGAC
1741 ----------+-------- 1759
     GTGGTGGTGATCCCAGCTG
572  H  H  H  *                574
```

FIG.3b-3

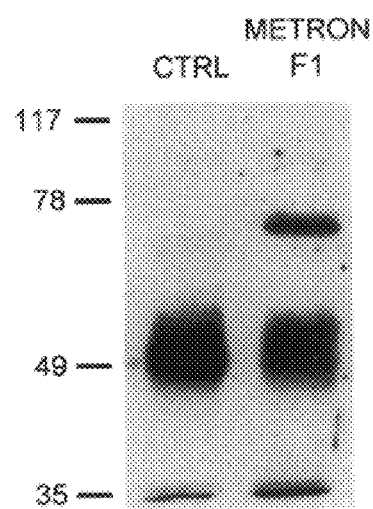
FIG.4
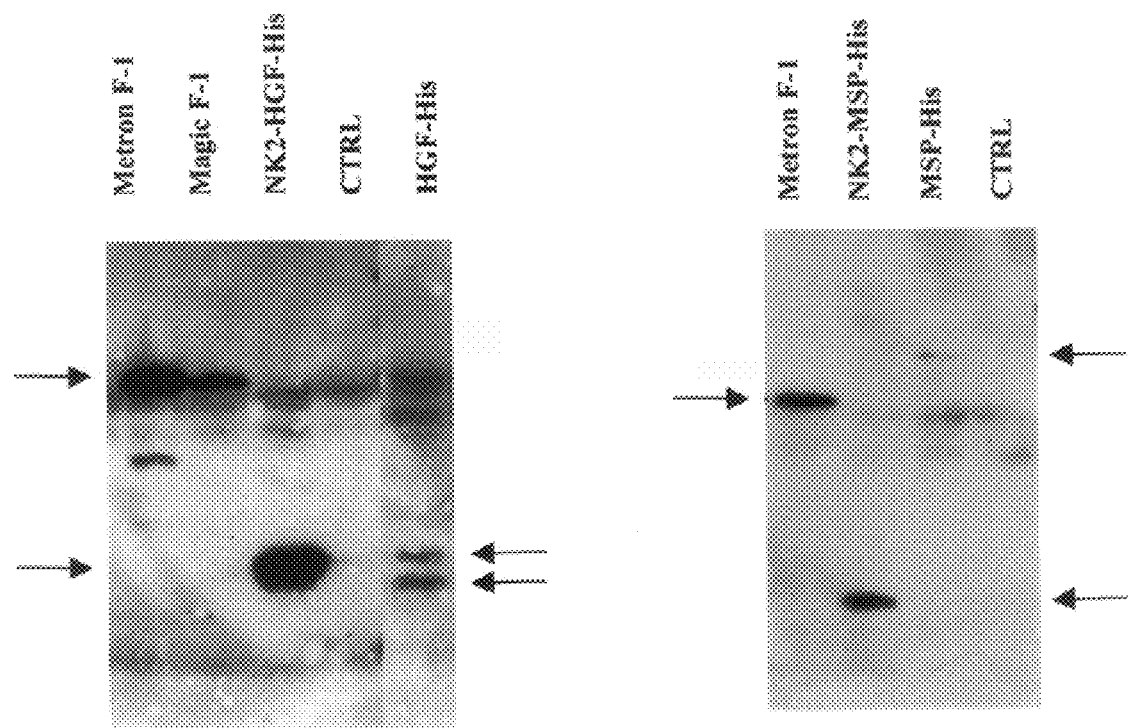
FIG.5a                    FIG.5b

SEQUENCE LISTING

<160> NUMBER OF SEQ ID NOS: 22

<210> SEQ ID NO 1
<211> LENGTH: 1725
<212> TYPE: DNA
<213> ORGANISM: Artificial Sequence
<220> FEATURE:
<223> OTHER INFORMATION: Magic F-1 DNA coding sequence

<400> SEQUENCE: 1

```
atgtgggtga ccaaactcct gccagccctg ctgctgcagc atgtcctcct gcatctcctc        60
ctgctcccca tcgccatccc ctatgcagag ggacaaagga aagaagaaa tacaattcat       120 gaattcaaaa aatcagcaaa gactaccta atcaaaatag atccagcact gaagataaaa        180
accaaaaaag tgaatactgc agaccaatgt gctaatagat gtactaggaa taaaggactt       240
ccattcactt gcaaggcttt tgtttttgat aaagcaagaa aacaatgcct ctggttcccc       300
ttcaatagca tgtcaagtgg agtgaaaaaa gaatttggcc atgaatttga cctctatgaa       360
aacaaagact acattagaaa ctgcatcatt ggtaaaggac gcagctacaa gggaacagta       420
tctatcacta agagtggcat caaatgtcag ccctggagtt ccatgatacc acacgaacac       480
agctatcggg gtaaagacct acaggaaaac tactgtcgaa atcctcgagg ggaagaaggg       540
ggaccctggt gtttcacaag caatccagag gtacgctacg aagtctgtga cattcctcag       600
tgttcagaag ttgaatgcat gacctgcaat ggggagagtt atcgaggtct catggatcat       660
acagaatcag gcaagatttg tcagcgctgg gatcatcaga caccacaccg gcacaaattc       720
ttgcctgaaa gatatcccga caagggcttt gatgataatt attgccgcaa tcccgatggc       780
cagccgaggc catggtgcta tactcttgac cctcacaccc gctgggagta ctgtgcaatt       840
aaaacatgcg ctgacaaagc ttcgggcggt ggcggttctg gtggcggtgg ctccggcggt       900
ggcggttctc tagagggaca aaggaaaaga agaaaatacaa ttcatgaatt caaaaaatca       960
gcaaagacta ccctaatcaa aatagatcca gcactgaaga taaaaccaa aaagtgaat      1020 actgcagacc aatgtgctaa tagatgtact aggaataaag gacttccatt cacttgcaag      1080
gcttttgttt ttgataaagc aagaaaacaa tgcctctggt tccccttcaa tagcatgtca      1140
agtggagtga aaaagaatt tggccatgaa tttgacctct atgaaaacaa agactacatt      1200
agaaactgca tcattggtaa aggacgcagc tacaagggaa cagtatctat cactaagagt      1260
ggcatcaaat gtcagccctg gagttccatg ataccacacg aacacagcta tcgggtaaa      1320 gacctacagg aaaactactg tcgaaatcct cgaggggaag aaggggacc ctggtgtttc      1380
```

```
acaagcaatc cagaggtacg ctacgaagtc tgtgacattc ctcagtgttc agaagttgaa   1440
tgcatgacct gcaatgggga gagttatcga ggtctcatgg atcatacaga atcaggcaag   1500
atttgtcagc gctgggatca tcagacacca caccggcaca aattcttgcc tgaaagatat   1560
cccgacaagg gctttgatga taattattgc cgcaatcccg atggccagcc gaggccatgg   1620
tgctatactc ttgaccctca cacccgctgg gagtactgtg caattaaaac atgcgctgac   1680
aaagctgacg acgacgacaa acaccaccac caccaccacc actag                   1725
```

<210> SEQ ID NO 2
<211> LENGTH: 574
<212> TYPE: PRT
<213> ORGANISM: Artificial Sequence
<220> FEATURE:
<223> OTHER INFORMATION: Magic F-1 recombinant protein obtained
      combining hairpin loop and kringle domains of human HGF and MSP

<400> SEQUENCE: 2

```
Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg
            180                 185                 190

Tyr Glu Val Cys Asp Ile Pro Gln Cys Ser Glu Val Glu Cys Met Thr
        195                 200                 205

Cys Asn Gly Glu Ser Tyr Arg Gly Leu Met Asp His Thr Glu Ser Gly
    210                 215                 220

Lys Ile Cys Gln Arg Trp Asp His Gln Thr Pro His Arg His Lys Phe
225                 230                 235                 240

Leu Pro Glu Arg Tyr Pro Asp Lys Gly Phe Asp Asp Asn Tyr Cys Arg
                245                 250                 255

Asn Pro Asp Gly Gln Pro Arg Pro Trp Cys Tyr Thr Leu Asp Pro His
            260                 265                 270

Thr Arg Trp Glu Tyr Cys Ala Ile Lys Thr Cys Ala Asp Lys Ala Ser
        275                 280                 285

Gly Gly Gly Gly Ser Gly Gly Gly Gly Ser Gly Gly Gly Gly Ser Leu
```

| | | | | | | | | | | | |
|---|---|---|---|---|---|---|---|---|---|---|---|
| | | 290 | | | | 295 | | | | 300 | |
| Glu | Gly | Gln | Arg | Lys | Arg | Arg | Asn | Thr | Ile | His | Glu | Phe | Lys | Lys | Ser |
| 305 | | | | | 310 | | | | | 315 | | | | | 320 |
| Ala | Lys | Thr | Thr | Leu | Ile | Lys | Ile | Asp | Pro | Ala | Leu | Lys | Ile | Lys | Thr |
| | | | | 325 | | | | | 330 | | | | | 335 | |
| Lys | Lys | Val | Asn | Thr | Ala | Asp | Gln | Cys | Ala | Asn | Arg | Cys | Thr | Arg | Asn |
| | | | 340 | | | | | 345 | | | | | 350 | | |
| Lys | Gly | Leu | Pro | Phe | Thr | Cys | Lys | Ala | Phe | Val | Phe | Asp | Lys | Ala | Arg |
| | | | 355 | | | | | 360 | | | | | 365 | | |
| Lys | Gln | Cys | Leu | Trp | Phe | Pro | Phe | Asn | Ser | Met | Ser | Ser | Gly | Val | Lys |
| | 370 | | | | | 375 | | | | | 380 | | | | |
| Lys | Glu | Phe | Gly | His | Glu | Phe | Asp | Leu | Tyr | Glu | Asn | Lys | Asp | Tyr | Ile |
| 385 | | | | | 390 | | | | | 395 | | | | | 400 |
| Arg | Asn | Cys | Ile | Ile | Gly | Lys | Gly | Arg | Ser | Tyr | Lys | Gly | Thr | Val | Ser |
| | | | | 405 | | | | | 410 | | | | | 415 | |
| Ile | Thr | Lys | Ser | Gly | Ile | Lys | Cys | Gln | Pro | Trp | Ser | Ser | Met | Ile | Pro |
| | | | 420 | | | | | 425 | | | | | 430 | | |
| His | Glu | His | Ser | Tyr | Arg | Gly | Lys | Asp | Leu | Gln | Glu | Asn | Tyr | Cys | Arg |
| | | 435 | | | | | 440 | | | | | 445 | | | |
| Asn | Pro | Arg | Gly | Glu | Glu | Gly | Gly | Pro | Trp | Cys | Phe | Thr | Ser | Asn | Pro |
| | 450 | | | | | 455 | | | | | 460 | | | | |
| Glu | Val | Arg | Tyr | Glu | Val | Cys | Asp | Ile | Pro | Gln | Cys | Ser | Glu | Val | Glu |
| 465 | | | | | 470 | | | | | 475 | | | | | 480 |
| Cys | Met | Thr | Cys | Asn | Gly | Glu | Ser | Tyr | Arg | Gly | Leu | Met | Asp | His | Thr |
| | | | | 485 | | | | | 490 | | | | | 495 | |
| Glu | Ser | Gly | Lys | Ile | Cys | Gln | Arg | Trp | Asp | His | Gln | Thr | Pro | His | Arg |
| | | | 500 | | | | | 505 | | | | | 510 | | |
| His | Lys | Phe | Leu | Pro | Glu | Arg | Tyr | Pro | Asp | Lys | Gly | Phe | Asp | Asp | Asn |
| | | 515 | | | | | 520 | | | | | 525 | | | |
| Tyr | Cys | Arg | Asn | Pro | Asp | Gly | Gln | Pro | Arg | Pro | Trp | Cys | Tyr | Thr | Leu |
| | 530 | | | | | 535 | | | | | 540 | | | | |
| Asp | Pro | His | Thr | Arg | Trp | Glu | Tyr | Cys | Ala | Ile | Lys | Thr | Cys | Ala | Asp |
| 545 | | | | | 550 | | | | | 555 | | | | | 560 |
| Lys | Ala | Asp | Asp | Asp | Lys | His | His | His | His | His | His | | | | |
| | | | | 565 | | | | | 570 | | | | | | |

<210> SEQ ID NO 3
<211> LENGTH: 1692
<212> TYPE: DNA
<213> ORGANISM: Artificial Sequence
<220> FEATURE:
<223> OTHER INFORMATION: Metron F-1 DNA coding sequence

<400> SEQUENCE: 3

| | | | | | |
|---|---|---|---|---|---|
| atgggtggc | tcccactcct | gctgcttctg | actcaatgct | tagggtccc | tgggcagcgc | 60 |
| tcgccattga | atgacttcca | agtgctccgg | ggcacagagc | tacagcacct | gctacatgcg | 120 |
| gtggtgcccg | ggccttggca | ggaggatgtg | gcagatgctg | aagagtgtgc | tggtcgctgt | 180 |
| gggcccttaa | tggactgccg | ggccttccac | tacaacgtga | gcagccatgg | ttgccaactg | 240 |
| ctgccatgga | ctcaacactc | gccccacacg | aggctgcggc | gttctgggcg | ctgtgacctc | 300 |
| ttccagaaga | aagactacgt | acggacctgc | atcatgaaca | atggggttgg | gtaccggggc | 360 |
| accatggcca | cgaccgtggg | tggcctgccc | tgccaggctt | ggagccacaa | gttcccgaat | 420 |
| gatcacaagt | acacgcccac | tctccggaat | ggcctggaag | agaacttctg | ccgtaaccct | 480 |

-continued

```
gatggcgacc ccggaggtcc ttggtgctac acaacagacc ctgctgtgcg cttccagagc     540
tgcggcatca atcctgccg ggaggccgcg tgtgtctggt gcaatggcga ggaataccgc     600
ggcgcggtag accgcacgga gtcagggcgc gagtgccagc gctgggatct tcagcacccg     660
caccagcacc ccttcgagcc gggcaagttc ctcgaccaag gtctggacga caactattgc     720
cggaatcctg acggctccga gcggccatgg tgctacacta cggatccgca gatcgagcga     780
gagttctgtg acctcccccg ctgcgggtcc gaggcacagc ccgcctcga ggcggtggc     840 ggttctggtg gcggtggctc cggcggtggc ggttctctag agggacaaag gaaaagaaga     900
aatacaattc atgaattcaa aaatcagca agactaccc taatcaaaat agatccagca     960
ctgaagataa aaccaaaaa agtgaatact gcagaccaat gtgctaatag atgtactagg    1020
aataaaggac ttccattcac ttgcaaggct tttgtttttg ataaagcaag aaaacaatgc    1080
ctctggttcc ccttcaatag catgtcaagt ggagtgaaaa agaatttgg ccatgaattt    1140 gacctctatg aaaacaaaga ctacattaga aactgcatca ttggtaaagg acgcagctac    1200
aagggaacag tatctatcac taagagtggc atcaaatgtc agccctggag ttccatgata    1260
ccacacgaac acagctatcg gggtaaagac ctacaggaaa actactgtcg aaatcctcga    1320
ggggaagaag ggggaccctg gtgtttcaca agcaatccag aggtacgcta cgaagtctgt    1380
gacattcctc agtgttcaga agttgaatgc atgacctgca atgggagag ttatcgaggt    1440 ctcatggatc atacagaatc aggcaagatt tgtcagcgct gggatcatca gacaccacac    1500
cggcacaaat tcttgcctga agatatccc gacaagggc ttgatgataa ttattgccgc    1560
aatcccgatg ccagccgag gccatggtgc tatactcttg accctcacac ccgctgggag    1620
tactgtgcaa ttaaaacatg cgctgacaaa gctgacgacg acgacaaaca ccaccaccac    1680
caccaccact ag                                                       1692
```

<210> SEQ ID NO 4
<211> LENGTH: 563
<212> TYPE: PRT
<213> ORGANISM: Artificial Sequence
<220> FEATURE:
<223> OTHER INFORMATION: Metron F-1 recombinant protein obtained
      combining hairpin loop and kringle domains of human HGF and MSP

<400> SEQUENCE: 4

```
Met Gly Trp Leu Pro Leu Leu Leu Leu Thr Gln Cys Leu Gly Val
1               5                   10                  15

Pro Gly Gln Arg Ser Pro Leu Asn Asp Phe Gln Val Leu Arg Gly Thr
            20                  25                  30

Glu Leu Gln His Leu Leu His Ala Val Pro Gly Pro Trp Gln Glu
        35                  40                  45

Asp Val Ala Asp Ala Glu Glu Cys Ala Gly Arg Cys Gly Pro Leu Met
    50                  55                  60

Asp Cys Arg Ala Phe His Tyr Asn Val Ser Ser His Gly Cys Gln Leu
65                  70                  75                  80

Leu Pro Trp Thr Gln His Ser Pro His Thr Arg Leu Arg Arg Ser Gly
                85                  90                  95

Arg Cys Asp Leu Phe Gln Lys Lys Asp Tyr Val Arg Thr Cys Ile Met
            100                 105                 110

Asn Asn Gly Val Gly Tyr Arg Gly Thr Met Ala Thr Thr Val Gly Gly
        115                 120                 125

Leu Pro Cys Gln Ala Trp Ser His Lys Phe Pro Asn Asp His Lys Tyr
    130                 135                 140
```

```
Thr Pro Thr Leu Arg Asn Gly Leu Glu Glu Asn Phe Cys Arg Asn Pro
145                 150                 155                 160

Asp Gly Asp Pro Gly Pro Trp Cys Tyr Thr Thr Asp Pro Ala Val
        165                 170                 175

Arg Phe Gln Ser Cys Gly Ile Lys Ser Cys Arg Glu Ala Ala Cys Val
                180                 185                 190

Trp Cys Asn Gly Glu Glu Tyr Arg Gly Ala Val Asp Arg Thr Glu Ser
            195                 200                 205

Gly Arg Glu Cys Gln Arg Trp Asp Leu Gln His Pro His Gln His Pro
    210                 215                 220

Phe Glu Pro Gly Lys Phe Leu Asp Gln Gly Leu Asp Asp Asn Tyr Cys
225                 230                 235                 240

Arg Asn Pro Asp Gly Ser Glu Arg Pro Trp Cys Tyr Thr Thr Asp Pro
                245                 250                 255

Gln Ile Glu Arg Glu Phe Cys Asp Leu Pro Arg Cys Gly Ser Glu Ala
                260                 265                 270

Gln Pro Arg Leu Glu Gly Gly Gly Ser Gly Gly Gly Gly Ser Gly
            275                 280                 285

Gly Gly Gly Ser Leu Glu Gly Gln Arg Lys Arg Arg Asn Thr Ile His
    290                 295                 300

Glu Phe Lys Lys Ser Ala Lys Thr Thr Leu Ile Lys Ile Asp Pro Ala
305                 310                 315                 320

Leu Lys Ile Lys Thr Lys Lys Val Asn Thr Ala Asp Gln Cys Ala Asn
                325                 330                 335

Arg Cys Thr Arg Asn Lys Gly Leu Pro Phe Thr Cys Lys Ala Phe Val
            340                 345                 350

Phe Asp Lys Ala Arg Lys Gln Cys Leu Trp Phe Pro Phe Asn Ser Met
        355                 360                 365

Ser Ser Gly Val Lys Lys Glu Phe Gly His Glu Phe Asp Leu Tyr Glu
    370                 375                 380

Asn Lys Asp Tyr Ile Arg Asn Cys Ile Ile Gly Lys Gly Arg Ser Tyr
385                 390                 395                 400

Lys Gly Thr Val Ser Ile Thr Lys Ser Gly Ile Lys Cys Gln Pro Trp
                405                 410                 415

Ser Ser Met Ile Pro His Glu His Ser Tyr Arg Gly Lys Asp Leu Gln
            420                 425                 430

Glu Asn Tyr Cys Arg Asn Pro Arg Gly Glu Glu Gly Gly Pro Trp Cys
        435                 440                 445

Phe Thr Ser Asn Pro Glu Val Arg Tyr Glu Val Cys Asp Ile Pro Gln
450                 455                 460

Cys Ser Glu Val Glu Cys Met Thr Cys Asn Gly Glu Ser Tyr Arg Gly
465                 470                 475                 480

Leu Met Asp His Thr Glu Ser Gly Lys Ile Cys Gln Arg Trp Asp His
                485                 490                 495

Gln Thr Pro His Arg His Lys Phe Leu Pro Glu Arg Tyr Pro Asp Lys
            500                 505                 510

Gly Phe Asp Asp Asn Tyr Cys Arg Asn Pro Asp Gly Gln Pro Arg Pro
        515                 520                 525

Trp Cys Tyr Thr Leu Asp Pro His Thr Arg Trp Glu Tyr Cys Ala Ile
    530                 535                 540

Lys Thr Cys Ala Asp Lys Ala Asp Asp Asp Lys His His His His
545                 550                 555                 560
```

His His His

<210> SEQ ID NO 5
<211> LENGTH: 36
<212> TYPE: DNA
<213> ORGANISM: Artificial Sequence
<220> FEATURE:
<223> OTHER INFORMATION: Oligonucleotide primer targeted to human MSP cDNA

<400> SEQUENCE: 5
cgcgcggaat tccaccatgg ggtggctccc actcct       36

<210> SEQ ID NO 6
<211> LENGTH: 36
<212> TYPE: DNA
<213> ORGANISM: Artificial Sequence
<220> FEATURE:
<223> OTHER INFORMATION: Oligonucleotide primer targeted to human MSP cDNA

<400> SEQUENCE: 6
cgcgcgctcg aggcggggct gtgcctcgga cccgca       36

<210> SEQ ID NO 7
<211> LENGTH: 36
<212> TYPE: DNA
<213> ORGANISM: Artificial Sequence
<220> FEATURE:
<223> OTHER INFORMATION: Oligonucleotide primer targeted to human HGF cDNA

<400> SEQUENCE: 7
cgcgcgtcta gagggacaaa ggaaaagaag aaatac       36

<210> SEQ ID NO 8
<211> LENGTH: 36
<212> TYPE: DNA
<213> ORGANISM: Artificial Sequence
<220> FEATURE:
<223> OTHER INFORMATION: Oligonucleotide primer targeted to human HGF cDNA

<400> SEQUENCE: 8
cgcgcgaagc tttgtcagcg catgttttaa ttgcac       36

<210> SEQ ID NO 9
<211> LENGTH: 50
<212> TYPE: DNA
<213> ORGANISM: Artificial Sequence
<220> FEATURE:
<223> OTHER INFORMATION: Oligonucleotide primer used to synthesize the Metron Factor-1 linker sequence

<400> SEQUENCE: 9
tcgagggcgg tggcggttct ggtggcggtg gctccggcgg tggcggttct       50

<210> SEQ ID NO 10
<211> LENGTH: 50
<212> TYPE: DNA
<213> ORGANISM: Artificial Sequence
<220> FEATURE:
<223> OTHER INFORMATION: Oligonucleotide primer used to synthesize the Metron Factor-1 linker sequence

<400> SEQUENCE: 10
ctagagaacc gccaccgccg gagccaccgc caccagaacc gccaccgccc       50

<210> SEQ ID NO 11
<211> LENGTH: 50
<212> TYPE: DNA
<213> ORGANISM: Artificial Sequence
<220> FEATURE:
<223> OTHER INFORMATION: Oligonucleotide primer used to insert the tag
      sequence in Metron Factor-1

<400> SEQUENCE: 11
agctgacgac gacgacaaac accaccacca ccaccaccac tagggtcgac           50

<210> SEQ ID NO 12
<211> LENGTH: 50
<212> TYPE: DNA
<213> ORGANISM: Artificial Sequence
<220> FEATURE:
<223> OTHER INFORMATION: Oligonucleotide primer used to insert the tag
      sequence in Metron Factor-1

<400> SEQUENCE: 12
agctgtcgac cctagtggtg gtggtggtgg tggtgtttgt cgtcgtcgtc           50

<210> SEQ ID NO 13
<211> LENGTH: 36
<212> TYPE: DNA
<213> ORGANISM: Artificial Sequence
<220> FEATURE:
<223> OTHER INFORMATION: Oligonucleotide primer targeted to human HGF
      cDNA

<400> SEQUENCE: 13
cgcgcgggat ccgccagccg ctccagcagc accatg                         36

<210> SEQ ID NO 14
<211> LENGTH: 36
<212> TYPE: DNA
<213> ORGANISM: Artificial Sequence
<220> FEATURE:
<223> OTHER INFORMATION: Oligonucleotide primer targeted to human HGF
      cDNA

<400> SEQUENCE: 14
cgcgcgaagc tttgtcagcg catgttttaa ttgcac                         36

<210> SEQ ID NO 15
<211> LENGTH: 52
<212> TYPE: DNA
<213> ORGANISM: Artificial Sequence
<220> FEATURE:
<223> OTHER INFORMATION: Oligonucleotide primer used to synthesize the
      Magic Factor-1 linker sequence

<400> SEQUENCE: 15
agcttcgggc ggtggcggtt ctggtggcgg tggctccggc ggtggcggtt ct       52

<210> SEQ ID NO 16
<211> LENGTH: 52
<212> TYPE: DNA
<213> ORGANISM: Artificial Sequence
<220> FEATURE:
<223> OTHER INFORMATION: Oligonucleotide primer used to synthesize the
      Magic Factor-1 linker sequence

<400> SEQUENCE: 16
ctagagaacc gccaccgccg gagccaccgc caccagaacc gccaccgccc ga       52

<210> SEQ ID NO 17
<211> LENGTH: 2172
<212> TYPE: DNA
<213> ORGANISM: Homo sapiens
<220> FEATURE:
<221> NAME/KEY: CDS
<222> LOCATION: (1)..(2172)
<223> OTHER INFORMATION:

<400> SEQUENCE: 17

| | | | | | | | | | | | | | | | | |
|---|---|---|---|---|---|---|---|---|---|---|---|---|---|---|---|---|
| atg | tgg | gtg | acc | aaa | ctc | ctg | cca | gcc | ctg | ctg | ctg | cag | cat | gtc | ctc | 48 |
| Met | Trp | Val | Thr | Lys | Leu | Leu | Pro | Ala | Leu | Leu | Leu | Gln | His | Val | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ctg | cat | ctc | ctc | ctg | ctc | ccc | atc | gcc | atc | ccc | tat | gca | gag | gga | caa | 96 |
| Leu | His | Leu | Leu | Leu | Leu | Pro | Ile | Ala | Ile | Pro | Tyr | Ala | Glu | Gly | Gln | |
| | | 20 | | | | | 25 | | | | | 30 | | | | |

| | | | | | | | | | | | | | | | | |
|---|---|---|---|---|---|---|---|---|---|---|---|---|---|---|---|---|
| agg | aaa | aga | aga | aat | aca | att | cat | gaa | ttc | aaa | aaa | tca | gca | aag | act | 144 |
| Arg | Lys | Arg | Arg | Asn | Thr | Ile | His | Glu | Phe | Lys | Lys | Ser | Ala | Lys | Thr | |
| | | | 35 | | | | | 40 | | | | | 45 | | | |

| | | | | | | | | | | | | | | | | |
|---|---|---|---|---|---|---|---|---|---|---|---|---|---|---|---|---|
| acc | cta | atc | aaa | ata | gat | cca | gca | ctg | aag | ata | aaa | acc | aaa | aaa | gtg | 192 |
| Thr | Leu | Ile | Lys | Ile | Asp | Pro | Ala | Leu | Lys | Ile | Lys | Thr | Lys | Lys | Val | |
| | 50 | | | | | 55 | | | | | 60 | | | | | |

| | | | | | | | | | | | | | | | | |
|---|---|---|---|---|---|---|---|---|---|---|---|---|---|---|---|---|
| aat | act | gca | gac | caa | tgt | gct | aat | aga | tgt | act | agg | aat | aaa | gga | ctt | 240 |
| Asn | Thr | Ala | Asp | Gln | Cys | Ala | Asn | Arg | Cys | Thr | Arg | Asn | Lys | Gly | Leu | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| cca | ttc | act | tgc | aag | gct | ttt | gtt | ttt | gat | aaa | gca | aga | aaa | caa | tgc | 288 |
| Pro | Phe | Thr | Cys | Lys | Ala | Phe | Val | Phe | Asp | Lys | Ala | Arg | Lys | Gln | Cys | |
| | | | | 85 | | | | | 90 | | | | | 95 | | |

| | | | | | | | | | | | | | | | | |
|---|---|---|---|---|---|---|---|---|---|---|---|---|---|---|---|---|
| ctc | tgg | ttc | ccc | ttc | aat | agc | atg | tca | agt | gga | gtg | aaa | aaa | gaa | ttt | 336 |
| Leu | Trp | Phe | Pro | Phe | Asn | Ser | Met | Ser | Ser | Gly | Val | Lys | Lys | Glu | Phe | |
| | | | 100 | | | | | 105 | | | | | 110 | | | |

| | | | | | | | | | | | | | | | | |
|---|---|---|---|---|---|---|---|---|---|---|---|---|---|---|---|---|
| ggc | cat | gaa | ttt | gac | ctc | tat | gaa | aac | aaa | gac | tac | att | aga | aac | tgc | 384 |
| Gly | His | Glu | Phe | Asp | Leu | Tyr | Glu | Asn | Lys | Asp | Tyr | Ile | Arg | Asn | Cys | |
| | | 115 | | | | | 120 | | | | | 125 | | | | |

| | | | | | | | | | | | | | | | | |
|---|---|---|---|---|---|---|---|---|---|---|---|---|---|---|---|---|
| atc | att | ggt | aaa | gga | cgc | agc | tac | aag | gga | aca | gta | tct | atc | act | aag | 432 |
| Ile | Ile | Gly | Lys | Gly | Arg | Ser | Tyr | Lys | Gly | Thr | Val | Ser | Ile | Thr | Lys | |
| | | 130 | | | | | 135 | | | | | 140 | | | | |

| | | | | | | | | | | | | | | | | |
|---|---|---|---|---|---|---|---|---|---|---|---|---|---|---|---|---|
| agt | ggc | atc | aaa | tgt | cag | ccc | tgg | agt | tcc | atg | ata | cca | cac | gaa | cac | 480 |
| Ser | Gly | Ile | Lys | Cys | Gln | Pro | Trp | Ser | Ser | Met | Ile | Pro | His | Glu | His | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| agc | tat | cgg | ggt | aaa | gac | cta | cag | gaa | aac | tac | tgt | cga | aat | cct | cga | 528 |
| Ser | Tyr | Arg | Gly | Lys | Asp | Leu | Gln | Glu | Asn | Tyr | Cys | Arg | Asn | Pro | Arg | |
| | | | | 165 | | | | | 170 | | | | | 175 | | |

| | | | | | | | | | | | | | | | | |
|---|---|---|---|---|---|---|---|---|---|---|---|---|---|---|---|---|
| ggg | gaa | gaa | ggg | gga | ccc | tgg | tgt | ttc | aca | agc | aat | cca | gag | gta | cgc | 576 |
| Gly | Glu | Glu | Gly | Gly | Pro | Trp | Cys | Phe | Thr | Ser | Asn | Pro | Glu | Val | Arg | |
| | | | 180 | | | | | 185 | | | | | 190 | | | |

| | | | | | | | | | | | | | | | | |
|---|---|---|---|---|---|---|---|---|---|---|---|---|---|---|---|---|
| tac | gaa | gtc | tgt | gac | att | cct | cag | tgt | tca | gaa | gtt | gaa | tgc | atg | acc | 624 |
| Tyr | Glu | Val | Cys | Asp | Ile | Pro | Gln | Cys | Ser | Glu | Val | Glu | Cys | Met | Thr | |
| | | 195 | | | | | 200 | | | | | 205 | | | | |

| | | | | | | | | | | | | | | | | |
|---|---|---|---|---|---|---|---|---|---|---|---|---|---|---|---|---|
| tgc | aat | ggg | gag | agt | tat | cga | ggt | ctc | atg | gat | cat | aca | gaa | tca | ggc | 672 |
| Cys | Asn | Gly | Glu | Ser | Tyr | Arg | Gly | Leu | Met | Asp | His | Thr | Glu | Ser | Gly | |
| | 210 | | | | | 215 | | | | | 220 | | | | | |

| | | | | | | | | | | | | | | | | |
|---|---|---|---|---|---|---|---|---|---|---|---|---|---|---|---|---|
| aag | att | tgt | cag | cgc | tgg | gat | cat | cag | aca | cca | cac | cgg | cac | aaa | ttc | 720 |
| Lys | Ile | Cys | Gln | Arg | Trp | Asp | His | Gln | Thr | Pro | His | Arg | His | Lys | Phe | |
| 225 | | | | 230 | | | | | 235 | | | | | 240 | | |

| | | | | | | | | | | | | | | | | |
|---|---|---|---|---|---|---|---|---|---|---|---|---|---|---|---|---|
| ttg | cct | gaa | aga | tat | ccc | gac | aag | ggc | ttt | gat | gat | aat | tat | tgc | cgc | 768 |
| Leu | Pro | Glu | Arg | Tyr | Pro | Asp | Lys | Gly | Phe | Asp | Asp | Asn | Tyr | Cys | Arg | |
| | | | | 245 | | | | | 250 | | | | | 255 | | |

| | | | | | | | | | | | | | | | | |
|---|---|---|---|---|---|---|---|---|---|---|---|---|---|---|---|---|
| aat | ccc | gat | ggc | cag | ccg | agg | cca | tgg | tgc | tat | act | ctt | gac | cct | cac | 816 |
| Asn | Pro | Asp | Gly | Gln | Pro | Arg | Pro | Trp | Cys | Tyr | Thr | Leu | Asp | Pro | His | |
| | | | 260 | | | | | 265 | | | | | 270 | | | |

| | | |
|---|---|---|
| acc cgc tgg gag tac tgt gca att aaa aca tgc gct gac aat act atg<br>Thr Arg Trp Glu Tyr Cys Ala Ile Lys Thr Cys Ala Asp Asn Thr Met<br>            275                  280                  285 | 864 |
| aat gac act gat gtt cct ttg gaa aca act gaa tgc atc caa ggt caa<br>Asn Asp Thr Asp Val Pro Leu Glu Thr Thr Glu Cys Ile Gln Gly Gln<br>290                  295                  300 | 912 |
| gga gaa ggc tac agg ggc act gtc aat acc att tgg aat gga att cca<br>Gly Glu Gly Tyr Arg Gly Thr Val Asn Thr Ile Trp Asn Gly Ile Pro<br>305                  310                  315                  320 | 960 |
| tgt cag cgt tgg gat tct cag tat cct cac gag cat gac atg act cct<br>Cys Gln Arg Trp Asp Ser Gln Tyr Pro His Glu His Asp Met Thr Pro<br>            325                  330                  335 | 1008 |
| gaa aat ttc aag tgc aag gac cta cga gaa aat tac tgc cga aat cca<br>Glu Asn Phe Lys Cys Lys Asp Leu Arg Glu Asn Tyr Cys Arg Asn Pro<br>                  340                  345                  350 | 1056 |
| gat ggg tct gaa tca ccc tgg tgt ttt acc act gat cca aac atc cga<br>Asp Gly Ser Glu Ser Pro Trp Cys Phe Thr Thr Asp Pro Asn Ile Arg<br>            355                  360                  365 | 1104 |
| gtt ggc tac tgc tcc caa att cca aac tgt gat atg tca cat gga caa<br>Val Gly Tyr Cys Ser Gln Ile Pro Asn Cys Asp Met Ser His Gly Gln<br>            370                  375                  380 | 1152 |
| gat tgt tat cgt ggg aat ggc aaa aat tat atg ggc aac tta tcc caa<br>Asp Cys Tyr Arg Gly Asn Gly Lys Asn Tyr Met Gly Asn Leu Ser Gln<br>385                  390                  395                  400 | 1200 |
| aca aga tct gga cta aca tgt tca atg tgg gac aag aac atg gaa gac<br>Thr Arg Ser Gly Leu Thr Cys Ser Met Trp Asp Lys Asn Met Glu Asp<br>                  405                  410                  415 | 1248 |
| tta cat cgt cat atc ttc tgg gaa cca gat gca agt aag ctg aat gag<br>Leu His Arg His Ile Phe Trp Glu Pro Asp Ala Ser Lys Leu Asn Glu<br>            420                  425                  430 | 1296 |
| aat tac tgc cga aat cca gat gat gat gct cat gga ccc tgg tgc tac<br>Asn Tyr Cys Arg Asn Pro Asp Asp Asp Ala His Gly Pro Trp Cys Tyr<br>                  435                  440                  445 | 1344 |
| acg gga aat cca ctc att cct tgg gat tat tgc cct att tct cgt tgt<br>Thr Gly Asn Pro Leu Ile Pro Trp Asp Tyr Cys Pro Ile Ser Arg Cys<br>            450                  455                  460 | 1392 |
| gaa ggt gat acc aca cct aca ata gtc aat tta gac cat ccc gta ata<br>Glu Gly Asp Thr Thr Pro Thr Ile Val Asn Leu Asp His Pro Val Ile<br>465                  470                  475                  480 | 1440 |
| tct tgt gcc aaa acg aaa caa ttg cga gtt gta aat ggg att cca aca<br>Ser Cys Ala Lys Thr Lys Gln Leu Arg Val Val Asn Gly Ile Pro Thr<br>                  485                  490                  495 | 1488 |
| cga aca aac ata gga tgg atg gtt agt ttg aga tac aga aat aaa cat<br>Arg Thr Asn Ile Gly Trp Met Val Ser Leu Arg Tyr Arg Asn Lys His<br>            500                  505                  510 | 1536 |
| atc tgc gga gga tca ttg ata aag gag agt tgg gtt ctt act gca cga<br>Ile Cys Gly Gly Ser Leu Ile Lys Glu Ser Trp Val Leu Thr Ala Arg<br>            515                  520                  525 | 1584 |
| cag tgt ttc cct tct cga gac ttg aaa gat tat gaa gct tgg ctt gga<br>Gln Cys Phe Pro Ser Arg Asp Leu Lys Asp Tyr Glu Ala Trp Leu Gly<br>            530                  535                  540 | 1632 |
| att cat gat gtc cac gga aga gga gat gag aaa tgc aaa cag gtt ctc<br>Ile His Asp Val His Gly Arg Gly Asp Glu Lys Cys Lys Gln Val Leu<br>545                  550                  555                  560 | 1680 |
| aat gtt tcc cag ctg gta tat ggc cct gaa gga tca gat ctg gtt tta<br>Asn Val Ser Gln Leu Val Tyr Gly Pro Glu Gly Ser Asp Leu Val Leu<br>                  565                  570                  575 | 1728 |
| atg aag ctt gcc agg cct gct gtc ctg gat gat ttt gtt agt acg att<br>Met Lys Leu Ala Arg Pro Ala Val Leu Asp Asp Phe Val Ser Thr Ile | 1776 |

```
                      580                  585                  590
gat tta cct aat tat gga tgc aca att cct gaa aag acc agt tgc agt       1824
Asp Leu Pro Asn Tyr Gly Cys Thr Ile Pro Glu Lys Thr Ser Cys Ser
        595                 600                 605 gtt tat ggc tgg ggc tac act gga ttg atc aac tat gat ggc cta tta       1872
Val Tyr Gly Trp Gly Tyr Thr Gly Leu Ile Asn Tyr Asp Gly Leu Leu
    610                 615                 620 cga gtg gca cat ctc tat ata atg gga aat gag aaa tgc agc cag cat       1920
Arg Val Ala His Leu Tyr Ile Met Gly Asn Glu Lys Cys Ser Gln His
625                 630                 635                 640 cat cga ggg aag gtg act ctg aat gag tct gaa ata tgt gct ggg gct       1968
His Arg Gly Lys Val Thr Leu Asn Glu Ser Glu Ile Cys Ala Gly Ala
                645                 650                 655 gaa aag att gga tca gga cca tgt gag ggg gat tat ggt ggc cca ctt       2016
Glu Lys Ile Gly Ser Gly Pro Cys Glu Gly Asp Tyr Gly Gly Pro Leu
            660                 665                 670 gtt tgt gag caa cat aaa atg aga atg gtt ctt ggt gtc att gtt cct       2064
Val Cys Glu Gln His Lys Met Arg Met Val Leu Gly Val Ile Val Pro
        675                 680                 685 ggt cgt gga tgt gcc att cca aat cgt cct ggt att ttt gtc cga gta       2112
Gly Arg Gly Cys Ala Ile Pro Asn Arg Pro Gly Ile Phe Val Arg Val
    690                 695                 700 gca tat tat gca aaa tgg ata cac aaa att att tta aca tat aag gta       2160
Ala Tyr Tyr Ala Lys Trp Ile His Lys Ile Ile Leu Thr Tyr Lys Val
705                 710                 715                 720 cca cag tca tag                                                       2172
Pro Gln Ser <210> SEQ ID NO 18
<211> LENGTH: 723
<212> TYPE: PRT
<213> ORGANISM: Homo sapiens

<400> SEQUENCE: 18

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg
```

-continued

```
                180                 185                 190
Tyr Glu Val Cys Asp Ile Pro Gln Cys Ser Glu Val Glu Cys Met Thr
                195                 200                 205
Cys Asn Gly Glu Ser Tyr Arg Gly Leu Met Asp His Thr Glu Ser Gly
            210                 215                 220
Lys Ile Cys Gln Arg Trp Asp His Gln Thr Pro His Arg His Lys Phe
225                 230                 235                 240
Leu Pro Glu Arg Tyr Pro Asp Lys Gly Phe Asp Asp Asn Tyr Cys Arg
                245                 250                 255
Asn Pro Asp Gly Gln Pro Arg Pro Trp Cys Tyr Thr Leu Asp Pro His
            260                 265                 270
Thr Arg Trp Glu Tyr Cys Ala Ile Lys Thr Cys Ala Asp Asn Thr Met
            275                 280                 285
Asn Asp Thr Asp Val Pro Leu Glu Thr Thr Glu Cys Ile Gln Gly Gln
    290                 295                 300
Gly Glu Gly Tyr Arg Gly Thr Val Asn Thr Ile Trp Asn Gly Ile Pro
305                 310                 315                 320
Cys Gln Arg Trp Asp Ser Gln Tyr Pro His Glu His Asp Met Thr Pro
                325                 330                 335
Glu Asn Phe Lys Cys Lys Asp Leu Arg Glu Asn Tyr Cys Arg Asn Pro
            340                 345                 350
Asp Gly Ser Glu Ser Pro Trp Cys Phe Thr Thr Asp Pro Asn Ile Arg
            355                 360                 365
Val Gly Tyr Cys Ser Gln Ile Pro Asn Cys Asp Met Ser His Gly Gln
        370                 375                 380
Asp Cys Tyr Arg Gly Asn Gly Lys Asn Tyr Met Gly Asn Leu Ser Gln
385                 390                 395                 400
Thr Arg Ser Gly Leu Thr Cys Ser Met Trp Asp Lys Asn Met Glu Asp
                405                 410                 415
Leu His Arg His Ile Phe Trp Glu Pro Asp Ala Ser Lys Leu Asn Glu
                420                 425                 430
Asn Tyr Cys Arg Asn Pro Asp Asp Asp Ala His Gly Pro Trp Cys Tyr
            435                 440                 445
Thr Gly Asn Pro Leu Ile Pro Trp Asp Tyr Cys Pro Ile Ser Arg Cys
        450                 455                 460
Glu Gly Asp Thr Thr Pro Thr Ile Val Asn Leu Asp His Pro Val Ile
465                 470                 475                 480
Ser Cys Ala Lys Thr Lys Gln Leu Arg Val Val Asn Gly Ile Pro Thr
                485                 490                 495
Arg Thr Asn Ile Gly Trp Met Val Ser Leu Arg Tyr Arg Asn Lys His
                500                 505                 510
Ile Cys Gly Gly Ser Leu Ile Lys Glu Ser Trp Val Leu Thr Ala Arg
        515                 520                 525
Gln Cys Phe Pro Ser Arg Asp Leu Lys Asp Tyr Glu Ala Trp Leu Gly
    530                 535                 540
Ile His Asp Val His Gly Arg Gly Asp Glu Lys Cys Lys Gln Val Leu
545                 550                 555                 560
Asn Val Ser Gln Leu Val Tyr Gly Pro Glu Gly Ser Asp Leu Val Leu
                565                 570                 575
Met Lys Leu Ala Arg Pro Ala Val Leu Asp Asp Phe Val Ser Thr Ile
            580                 585                 590
Asp Leu Pro Asn Tyr Gly Cys Thr Ile Pro Glu Lys Thr Ser Cys Ser
    595                 600                 605
```

```
Val Tyr Gly Trp Gly Tyr Thr Gly Leu Ile Asn Tyr Asp Gly Leu Leu
    610             615                 620

Arg Val Ala His Leu Tyr Ile Met Gly Asn Glu Lys Cys Ser Gln His
625             630                 635                 640

His Arg Gly Lys Val Thr Leu Asn Glu Ser Glu Ile Cys Ala Gly Ala
            645                 650                 655

Glu Lys Ile Gly Ser Gly Pro Cys Glu Gly Asp Tyr Gly Gly Pro Leu
            660                 665                 670

Val Cys Glu Gln His Lys Met Arg Met Val Leu Gly Val Ile Val Pro
            675                 680                 685

Gly Arg Gly Cys Ala Ile Pro Asn Arg Pro Gly Ile Phe Val Arg Val
    690             695                 700

Ala Tyr Tyr Ala Lys Trp Ile His Lys Ile Ile Leu Thr Tyr Lys Val
705             710                 715                 720

Pro Gln Ser

<210> SEQ ID NO 19
<211> LENGTH: 2136
<212> TYPE: DNA
<213> ORGANISM: Homo sapiens
<220> FEATURE:
<221> NAME/KEY: CDS
<222> LOCATION: (1)..(2136)
<223> OTHER INFORMATION:

<400> SEQUENCE: 19 atg ggg tgg ctc cca ctc ctg ctg ctt ctg act caa tgc tta ggg gtc      48
Met Gly Trp Leu Pro Leu Leu Leu Leu Leu Thr Gln Cys Leu Gly Val
1               5                   10                  15 cct ggg cag cgc tcg cca ttg aat gac ttc caa gtg ctc cgg ggc aca      96
Pro Gly Gln Arg Ser Pro Leu Asn Asp Phe Gln Val Leu Arg Gly Thr
                20                  25                  30 gag cta cag cac ctg cta cat gcg gtg gtg ccc ggg cct tgg cag gag     144
Glu Leu Gln His Leu Leu His Ala Val Val Pro Gly Pro Trp Gln Glu
            35                  40                  45 gat gtg gca gat gct gaa gag tgt gct ggt cgc tgt ggg ccc tta atg     192
Asp Val Ala Asp Ala Glu Glu Cys Ala Gly Arg Cys Gly Pro Leu Met
        50                  55                  60 gac tgc cgg gcc ttc cac tac aac gtg agc agc cat ggt tgc caa ctg     240
Asp Cys Arg Ala Phe His Tyr Asn Val Ser Ser His Gly Cys Gln Leu
65                  70                  75                  80 ctg cca tgg act caa cac tcg ccc cac acg agg ctg cgg cgt tct ggg     288
Leu Pro Trp Thr Gln His Ser Pro His Thr Arg Leu Arg Arg Ser Gly
                85                  90                  95 cgc tgt gac ctc ttc cag aag aaa gac tac gta cgg acc tgc atc atg     336
Arg Cys Asp Leu Phe Gln Lys Lys Asp Tyr Val Arg Thr Cys Ile Met
                100                 105                 110 aac aat ggg gtt ggg tac cgg ggc acc atg gcc acg acc gtg ggt ggc     384
Asn Asn Gly Val Gly Tyr Arg Gly Thr Met Ala Thr Thr Val Gly Gly
            115                 120                 125 ctg ccc tgc cag gct tgg agc cac aag ttc ccg aat gat cac aag tac     432
Leu Pro Cys Gln Ala Trp Ser His Lys Phe Pro Asn Asp His Lys Tyr
        130                 135                 140 acg ccc act ctc cgg aat ggc ctg gaa gag aac ttc tgc cgt aac cct     480
Thr Pro Thr Leu Arg Asn Gly Leu Glu Glu Asn Phe Cys Arg Asn Pro
145                 150                 155                 160 gat ggc gac ccc gga ggt cct tgg tgc tac aca aca gac cct gct gtg     528
Asp Gly Asp Pro Gly Gly Pro Trp Cys Tyr Thr Thr Asp Pro Ala Val
                165                 170                 175
```

-continued

| | | |
|---|---|---|
| cgc ttc cag agc tgc ggc atc aaa tcc tgc cgg gag gcc gcg tgt gtc<br>Arg Phe Gln Ser Cys Gly Ile Lys Ser Cys Arg Glu Ala Ala Cys Val<br>180 185 190 | 576 | |
| tgg tgc aat ggc gag gaa tac cgc ggc gcg gta gac cgc acg gag tca<br>Trp Cys Asn Gly Glu Glu Tyr Arg Gly Ala Val Asp Arg Thr Glu Ser<br>195 200 205 | 624 | |
| ggg cgc gag tgc cag cgc tgg gat ctt cag cac ccg cac cag cac ccc<br>Gly Arg Glu Cys Gln Arg Trp Asp Leu Gln His Pro His Gln His Pro<br>210 215 220 | 672 | |
| ttc gag ccg ggc aag ttc ctc gac caa ggt ctg gac gac aac tat tgc<br>Phe Glu Pro Gly Lys Phe Leu Asp Gln Gly Leu Asp Asp Asn Tyr Cys<br>225 230 235 240 | 720 | |
| cgg aat cct gac ggc tcc gag cgg cca tgg tgc tac act acg gat ccg<br>Arg Asn Pro Asp Gly Ser Glu Arg Pro Trp Cys Tyr Thr Thr Asp Pro<br>245 250 255 | 768 | |
| cag atc gag cga gag ttc tgt gac ctc ccc cgc tgc ggg tcc gag gca<br>Gln Ile Glu Arg Glu Phe Cys Asp Leu Pro Arg Cys Gly Ser Glu Ala<br>260 265 270 | 816 | |
| cag ccc cgc caa gag gcc aca act gtc agc tgc ttc cgc ggg aag ggt<br>Gln Pro Arg Gln Glu Ala Thr Thr Val Ser Cys Phe Arg Gly Lys Gly<br>275 280 285 | 864 | |
| gag ggc tac cgg ggc aca gcc aat acc acc act gcg ggc gta cct tgc<br>Glu Gly Tyr Arg Gly Thr Ala Asn Thr Thr Thr Ala Gly Val Pro Cys<br>290 295 300 | 912 | |
| cag cgt tgg gac gcg caa atc ccg cat cag cac cga ttt acg cca gaa<br>Gln Arg Trp Asp Ala Gln Ile Pro His Gln His Arg Phe Thr Pro Glu<br>305 310 315 320 | 960 | |
| aaa tac gcg tgc aaa gac ctt cgg gag aac ttc tgc cgg aac ccc gac<br>Lys Tyr Ala Cys Lys Asp Leu Arg Glu Asn Phe Cys Arg Asn Pro Asp<br>325 330 335 | 1008 | |
| ggc tca gag gcg ccc tgg tgc ttc aca ctg cgg ccc ggc atg cgc gcg<br>Gly Ser Glu Ala Pro Trp Cys Phe Thr Leu Arg Pro Gly Met Arg Ala<br>340 345 350 | 1056 | |
| gcc ttt tgc tac cag atc cgg cgt tgt aca gac gac gtg cgg ccc cag<br>Ala Phe Cys Tyr Gln Ile Arg Arg Cys Thr Asp Asp Val Arg Pro Gln<br>355 360 365 | 1104 | |
| gac tgc tac cac ggc gca ggg gag cag tac cgc ggc acg gtc agc aag<br>Asp Cys Tyr His Gly Ala Gly Glu Gln Tyr Arg Gly Thr Val Ser Lys<br>370 375 380 | 1152 | |
| acc cgc aag ggt gtc cag tgc cag cgc tgg tcc gct gag acg ccg cac<br>Thr Arg Lys Gly Val Gln Cys Gln Arg Trp Ser Ala Glu Thr Pro His<br>385 390 395 400 | 1200 | |
| aag ccg cag ttc acg ttt acc tcc gaa ccg cat gca caa ctg gag gag<br>Lys Pro Gln Phe Thr Phe Thr Ser Glu Pro His Ala Gln Leu Glu Glu<br>405 410 415 | 1248 | |
| aac ttc tgc cgg aac cca gat ggg gat agc cat ggg ccc tgg tgc tac<br>Asn Phe Cys Arg Asn Pro Asp Gly Asp Ser His Gly Pro Trp Cys Tyr<br>420 425 430 | 1296 | |
| acg atg gac cca agg acc cca ttc gac tac tgt gcc ctg cga cgc tgc<br>Thr Met Asp Pro Arg Thr Pro Phe Asp Tyr Cys Ala Leu Arg Arg Cys<br>435 440 445 | 1344 | |
| gct gat gac cag ccg cca tca atc ctg gac ccc cca gac cag gtg cag<br>Ala Asp Asp Gln Pro Pro Ser Ile Leu Asp Pro Pro Asp Gln Val Gln<br>450 455 460 | 1392 | |
| ttt gag aag tgt ggc aag agg gtg gat cgg ctg gat cag cgg cgt tcc<br>Phe Glu Lys Cys Gly Lys Arg Val Asp Arg Leu Asp Gln Arg Arg Ser<br>465 470 475 480 | 1440 | |
| aag ctg cgc gtg gtt ggg ggc cat ccg ggc aac tca ccc tgg aca gtc<br>Lys Leu Arg Val Val Gly Gly His Pro Gly Asn Ser Pro Trp Thr Val<br>485 490 495 | 1488 | |

-continued

```
agc ttg cgg aat cgg cag ggc cag cat ttc tgc ggg ggg tct cta gtg       1536
Ser Leu Arg Asn Arg Gln Gly Gln His Phe Cys Gly Gly Ser Leu Val
        500                 505                 510 aag gag cag tgg ata ctg act gcc cgg cag tgc ttc tcc tcc tgc cat       1584
Lys Glu Gln Trp Ile Leu Thr Ala Arg Gln Cys Phe Ser Ser Cys His
515                 520                 525 atg cct ctc acg ggc tat gag gta tgg ttg ggc acc ctg ttc cag aac       1632
Met Pro Leu Thr Gly Tyr Glu Val Trp Leu Gly Thr Leu Phe Gln Asn
    530                 535                 540 cca cag cat gga gag cca agc cta cag cgg gtc cca gta gcc aag atg       1680
Pro Gln His Gly Glu Pro Ser Leu Gln Arg Val Pro Val Ala Lys Met
545                 550                 555                 560 gtg tgt ggg ccc tca ggc tcc cag ctt gtc ctg ctc aag ctg gag aga       1728
Val Cys Gly Pro Ser Gly Ser Gln Leu Val Leu Leu Lys Leu Glu Arg
            565                 570                 575 tct gtg acc ctg aac cag cgt gtg gcc ctg atc tgc ctg ccc cct gaa       1776
Ser Val Thr Leu Asn Gln Arg Val Ala Leu Ile Cys Leu Pro Pro Glu
        580                 585                 590 tgg tat gtg gtg cct cca ggg acc aag tgt gag att gca ggc tgg ggt       1824
Trp Tyr Val Val Pro Pro Gly Thr Lys Cys Glu Ile Ala Gly Trp Gly
    595                 600                 605 gag acc aaa ggt acg ggt aat gac aca gtc cta aat gtg gcc ttt ctg       1872
Glu Thr Lys Gly Thr Gly Asn Asp Thr Val Leu Asn Val Ala Phe Leu
610                 615                 620 aat gtt atc tcc aac cag gag tgt aac atc aag cac cga gga cgt gtg       1920
Asn Val Ile Ser Asn Gln Glu Cys Asn Ile Lys His Arg Gly Arg Val
625                 630                 635                 640 cgg gag agt gag atg tgc act gag gga ctg ttg gcc cct gtg ggg gcc       1968
Arg Glu Ser Glu Met Cys Thr Glu Gly Leu Leu Ala Pro Val Gly Ala
            645                 650                 655 tgt gag ggt gac tac ggg ggc cca ctt gcc tgc ttt acc cac aac tgc       2016
Cys Glu Gly Asp Tyr Gly Gly Pro Leu Ala Cys Phe Thr His Asn Cys
        660                 665                 670 tgg gtc ctg gaa gga att ata atc ccc aac cga gta tgc gca agg tcc       2064
Trp Val Leu Glu Gly Ile Ile Ile Pro Asn Arg Val Cys Ala Arg Ser
    675                 680                 685 cgc tgg cca gct gtc ttc acg cgt gtc tct gtg ttt gtg gac tgg att       2112
Arg Trp Pro Ala Val Phe Thr Arg Val Ser Val Phe Val Asp Trp Ile
690                 695                 700 cac aag gtc atg aga ctg ggt tag                                       2136
His Lys Val Met Arg Leu Gly
705                 710

<210> SEQ ID NO 20
<211> LENGTH: 711
<212> TYPE: PRT
<213> ORGANISM: Homo sapiens

<400> SEQUENCE: 20

Met Gly Trp Leu Pro Leu Leu Leu Leu Thr Gln Cys Leu Gly Val
1               5                   10                  15

Pro Gly Gln Arg Ser Pro Leu Asn Asp Phe Gln Val Leu Arg Gly Thr
            20                  25                  30

Glu Leu Gln His Leu Leu His Ala Val Val Pro Gly Pro Trp Gln Glu
        35                  40                  45

Asp Val Ala Asp Ala Glu Glu Cys Ala Gly Arg Cys Gly Pro Leu Met
    50                  55                  60

Asp Cys Arg Ala Phe His Tyr Asn Val Ser Ser His Gly Cys Gln Leu
65                  70                  75                  80
```

-continued

```
Leu Pro Trp Thr Gln His Ser Pro His Thr Arg Leu Arg Arg Ser Gly
                85                  90                  95

Arg Cys Asp Leu Phe Gln Lys Lys Asp Tyr Val Arg Thr Cys Ile Met
            100                 105                 110

Asn Asn Gly Val Gly Tyr Arg Gly Thr Met Ala Thr Val Gly Gly
        115                 120                 125

Leu Pro Cys Gln Ala Trp Ser His Lys Phe Pro Asn Asp His Lys Tyr
    130                 135                 140

Thr Pro Thr Leu Arg Asn Gly Leu Glu Glu Asn Phe Cys Arg Asn Pro
145                 150                 155                 160

Asp Gly Asp Pro Gly Gly Pro Trp Cys Tyr Thr Thr Asp Pro Ala Val
                165                 170                 175

Arg Phe Gln Ser Cys Gly Ile Lys Ser Cys Arg Glu Ala Ala Cys Val
            180                 185                 190

Trp Cys Asn Gly Glu Glu Tyr Arg Gly Ala Val Asp Arg Thr Glu Ser
        195                 200                 205

Gly Arg Glu Cys Gln Arg Trp Asp Leu Gln His Pro His Gln His Pro
    210                 215                 220

Phe Glu Pro Gly Lys Phe Leu Asp Gln Gly Leu Asp Asp Asn Tyr Cys
225                 230                 235                 240

Arg Asn Pro Asp Gly Ser Glu Arg Pro Trp Cys Tyr Thr Thr Asp Pro
                245                 250                 255

Gln Ile Glu Arg Glu Phe Cys Asp Leu Pro Arg Cys Gly Ser Glu Ala
            260                 265                 270

Gln Pro Arg Gln Glu Ala Thr Thr Val Ser Cys Phe Arg Gly Lys Gly
        275                 280                 285

Glu Gly Tyr Arg Gly Thr Ala Asn Thr Thr Thr Ala Gly Val Pro Cys
    290                 295                 300

Gln Arg Trp Asp Ala Gln Ile Pro His Gln His Arg Phe Thr Pro Glu
305                 310                 315                 320

Lys Tyr Ala Cys Lys Asp Leu Arg Glu Asn Phe Cys Arg Asn Pro Asp
                325                 330                 335

Gly Ser Glu Ala Pro Trp Cys Phe Thr Leu Arg Pro Gly Met Arg Ala
            340                 345                 350

Ala Phe Cys Tyr Gln Ile Arg Arg Cys Thr Asp Asp Val Arg Pro Gln
        355                 360                 365

Asp Cys Tyr His Gly Ala Gly Glu Gln Tyr Arg Gly Thr Val Ser Lys
    370                 375                 380

Thr Arg Lys Gly Val Gln Cys Gln Arg Trp Ser Ala Glu Thr Pro His
385                 390                 395                 400

Lys Pro Gln Phe Thr Phe Thr Ser Glu Pro His Ala Gln Leu Glu Glu
                405                 410                 415

Asn Phe Cys Arg Asn Pro Asp Gly Asp Ser His Gly Pro Trp Cys Tyr
            420                 425                 430

Thr Met Asp Pro Arg Thr Pro Phe Asp Tyr Cys Ala Leu Arg Arg Cys
        435                 440                 445

Ala Asp Asp Gln Pro Pro Ser Ile Leu Asp Pro Pro Asp Gln Val Gln
    450                 455                 460

Phe Glu Lys Cys Gly Lys Arg Val Asp Arg Leu Asp Gln Arg Arg Ser
465                 470                 475                 480

Lys Leu Arg Val Val Gly Gly His Pro Gly Asn Ser Pro Trp Thr Val
                485                 490                 495

Ser Leu Arg Asn Arg Gln Gly Gln His Phe Cys Gly Gly Ser Leu Val
```

-continued

```
                500              505              510
Lys Glu Gln Trp Ile Leu Thr Ala Arg Gln Cys Phe Ser Ser Cys His
            515                  520              525

Met Pro Leu Thr Gly Tyr Glu Val Trp Leu Gly Thr Leu Phe Gln Asn
    530                  535                  540

Pro Gln His Gly Glu Pro Ser Leu Gln Arg Val Pro Val Ala Lys Met
545                  550                  555                  560

Val Cys Gly Pro Ser Gly Ser Gln Leu Val Leu Lys Leu Glu Arg
                565                  570                  575

Ser Val Thr Leu Asn Gln Arg Val Ala Leu Ile Cys Leu Pro Pro Glu
            580                  585                  590

Trp Tyr Val Val Pro Pro Gly Thr Lys Cys Glu Ile Ala Gly Trp Gly
        595                  600                  605

Glu Thr Lys Gly Thr Gly Asn Asp Thr Val Leu Asn Val Ala Phe Leu
    610                  615                  620

Asn Val Ile Ser Asn Gln Glu Cys Asn Ile Lys His Arg Gly Arg Val
625                  630                  635                  640

Arg Glu Ser Glu Met Cys Thr Glu Gly Leu Leu Ala Pro Val Gly Ala
                645                  650                  655

Cys Glu Gly Asp Tyr Gly Gly Pro Leu Ala Cys Phe Thr His Asn Cys
            660                  665                  670

Trp Val Leu Glu Gly Ile Ile Ile Pro Asn Arg Val Cys Ala Arg Ser
        675                  680                  685

Arg Trp Pro Ala Val Phe Thr Arg Val Ser Val Phe Val Asp Trp Ile
    690                  695                  700

His Lys Val Met Arg Leu Gly
705                  710

<210> SEQ ID NO 21
<211> LENGTH: 1709
<212> TYPE: DNA
<213> ORGANISM: Artificial Sequence
<220> FEATURE:
<223> OTHER INFORMATION: Metron F-1

<400> SEQUENCE: 21
gaattccacc atggggtggc tcccactcct gctgcttctg actcaatgct tagggtccc      60 tgggcagcgc tcgccattga atgacttcca agtgctccgg ggcacagagc tacagcacct     120
gctacatgcg gtggtgcccg ggccttggca ggaggatgtg gcagatgctg aagagtgtgc     180
tggtcgctgt gggcccttaa tggactgccg ggccttccac tacaacgtga gcagccatgg     240
ttgccaactg ctgccatgga ctcaacactc gccccacacg aggctgcggc gttctgggcg     300
ctgtgacctc ttccagaaga aagactacgt acggacctgc atcatgaaca atggggttgg     360
gtaccggggc accatggcca cgaccgtggg tggcctgccc tgccaggctt ggagccacaa     420
gttcccgaat gatcacaagt acacgcccac tctccggaat ggcctggaag agaacttctg     480
ccgtaaccct gatggcgacc ccggaggtcc ttggtgctac acaacagacc tgctgtgcg     540 cttccagagc tgcggcatca atcctgccg ggaggccgcg tgtgtctggt gcaatggcga     600
ggaataccgc ggcgcggtag accgcacgga gtcaggcgc gagtgccagc gctgggatct     660
tcagcacccg caccagcacc ccttcgagcc gggcaagttc ctcgaccaag gtctggacga     720
caactattgc cggaatcctg acggctccga gcggccatgg tgctacacta cggatccgca     780
gatcgagcga gagttctgtg acctcccccg ctgcgggtcc gaggcacagc cccgcctcga     840
```

-continued

```
gggcggtggc ggttctggtg gcggtggctc cggcggtggc ggttctctag agggacaaag      900
gaaaagaaga aatacaattc atgaattcaa aaaatcagca aagactaccc taatcaaaat      960
agatccagca ctgaagataa aaccaaaaa agtgaatact gcagaccaat gtgctaatag      1020
atgtactagg aataaaggac ttccattcac ttgcaaggct tttgtttttg ataaagcaag      1080
aaaacaatgc ctctggttcc ccttcaatag catgtcaagt ggagtgaaaa agaatttgg       1140
ccatgaattt gacctctatg aaaacaaaga ctacattaga aactgcatca ttggtaaagg      1200
acgcagctac aagggaacag tatctatcac taagagtggc atcaaatgtc agccctggag      1260
ttccatgata ccacacgaac acagctatcg ggtaaagac ctacaggaaa actactgtcg       1320
aaatcctcga ggggaagaag ggggaccctg tgtttcaca agcaatccag aggtacgcta       1380
cgaagtctgt gacattcctc agtgttcaga agttgaatgc atgacctgca atggggagag      1440
ttatcgaggt ctcatggatc atacagaatc aggcaagatt tgtcagcgct gggatcatca      1500
gacaccacac cggcacaaat tcttgcctga agatatccc gacaagggct ttgatgataa       1560
ttattgccgc aatcccgatg ccagccgag gccatggtgc tatactcttg accctcacac       1620
ccgctgggag tactgtgcaa ttaaaacatg cgctgacaaa gctgacgacg acgacaaaca      1680
ccaccaccac caccaccact agggtcgac                                         1709
```

<210> SEQ ID NO 22
<211> LENGTH: 1759
<212> TYPE: DNA
<213> ORGANISM: Artificial Sequence
<220> FEATURE:
<223> OTHER INFORMATION: Magic F-1

<400> SEQUENCE: 22

```
ggatccgcca gcccgtccag cagcaccatg tgggtgacca actcctgcc agccctgctg       60
ctgcagcatg tcctcctgca tctcctcctg ctccccatcg ccatcccta tgcagaggga     120
caaggaaaa gagaaatac aattcatgaa ttcaaaaaat cagcaaagac taccctaatc     180
aaatagatc cagcactgaa gataaaaacc aaaaagtga atactgcaga ccaatgtgct     240
aatagatgta ctaggaataa aggcttcca ttcacttgca aggcttttgt ttttgataaa     300
gcaagaaaac aatgcctctg gttccccttc aatagcatgt caagtggagt gaaaaagaa     360
tttggccatg aatttgacct ctatgaaaac aaagactaca ttagaaactg catcattggt     420
aaaggacgca gctacaaggg aacagtatct atcactaaga gtggcatcaa atgtcagccc     480
tggagttcca tgataccaca cgaacacagc tatcgggta agacctaca ggaaaactac      540
tgtcgaaatc ctcagggga agaaggggga ccctggtgtt tcacaagcaa tccagaggta     600
cgctacgaag tctgtgacat tcctcagtgt tcagaagttg aatgcatgac ctgcaatggg     660
gagagttatc gaggtctcat ggatcataca gaatcaggca gatttgtca gcgctgggat    720
catcagacac cacaccggca caattcttg cctgaaagat atcccgacaa gggctttgat    780
gataattatt gccgcaatcc cgatggcag ccgaggccat ggtgctatac tcttgacct      840
cacaccgct gggagtactg tgcaattaaa acatgcgctg acaaagcttc gggcggtggc     900
ggttctggtg gcggtggctc cggcggtggc ggttctctag agggacaaag gaaaagaaga     960
aatacaattc atgaattcaa aaaatcagca agactaccc taatcaaat agatccagca     1020
ctgaagataa aaccaaaaa agtgaatact gcagaccaat gtgctaatag atgtactagg     1080
aataaaggac ttccattcac ttgcaaggct tttgtttttg ataaagcaag aaaacaatgc     1140
ctctggttcc ccttcaatag catgtcaagt ggagtgaaaa agaatttgg ccatgaattt     1200
```

-continued

```
gacctctatg aaaacaaaga ctacattaga aactgcatca ttggtaaagg acgcagctac    1260
aagggaacag tatctatcac taagagtggc atcaaatgtc agccctggag ttccatgata    1320
ccacacgaac acagctatcg gggtaaagac ctacaggaaa actactgtcg aaatcctcga    1380
ggggaagaag ggggaccctg gtgtttcaca agcaatccag aggtacgcta cgaagtctgt    1440
gacattcctc agtgttcaga agttgaatgc atgacctgca atggggagag ttatcgaggt    1500
ctcatggatc atacagaatc aggcaagatt tgtcagcgct gggatcatca gacaccacac    1560
cggcacaaat tcttgcctga aagatatccc gacaagggct ttgatgataa ttattgccgc    1620
aatcccgatg gccagccgag gccatggtgc tatactcttg accctcacac ccgctgggag    1680
tactgtgcaa ttaaaacatg cgctgacaaa gctgacgacg acgacaaaca ccaccaccac    1740
caccaccact agggtcgac                                                  1759
```

RECOMBINANT PROTEINS DERIVED FROM HGF AND MSP

This application is the national phase under 35 U.S.C. §371 of PCT International Application No. PCT/EP99/00478 which has an International filing date of Jan. 27, 1999, which designated the United States of America, and was published on Aug. 5, 1999 as International Publication No. WO 99/38967.

FIELD OF THE INVENTION

The present invention relates to recombinant proteins obtained from the combination of structural domains derived from the a subunits of hepatocyte growth factor (HGF) and macrophage stimulating protein (MSP).

In particular, the engineered factors of the invention are obtained by combination of the hairpin loop and kringle domains of the α chains of HGF and/or MSP, so as to obtain a structure having two superdomains with an intervening linker sequence. Moreover, the invention relates to DNA sequences encoding the above mentioned recombinant proteins, to the expression vectors comprising said DNA sequences and to host cells containing said expression vectors. The recombinant proteins of the present invention are biologically active, and their activity can be measured by determination of their ability to induce activation of the Met tyrosine kinase receptor, their "scattering" effect on epithelial cells, and their protective effect against cell death induced by chemotherapic drugs (vide infra). Therefore, these molecules can conveniently be used to prevent or treat the toxic side effects of the chemotherapeutical treatment of tumours, and to reduce iatrogenic cell damage induced by other types of drugs.

TECHNOLOGICAL BACKGROUND

Hepatocyte Growth Factor (HGF) and Macrophage Stimulating Protein (MSP) are highly related proteins both structurally and functionally (FIGS. 1 and 2). Both these factors are secreted as an inactive precursor, which is processed by specific proteases which recognise a cleavage site inside the molecule, dividing the protein in two subunits. These subunits, named α chain and β chain, are linked by a disulphide bond. Thus, the mature factor is an α-β dimeric protein. Only the mature (dimeric) form of the factor is able to activate its receptor at the surface of the target cells (the Met tyrosine kinase in the case of HGF and the Ron tyrosine kinase in the case of MSP) and therefore to mediate biological responses (Naldini, L. et al., 1992, EMBO J. 11: 4825–4833; Wang, M. et al., 1994, J. Biol. Chem. 269; 3436–3440; Bottaro, D. et al., 1991, Science 25: 802–804; Naldini, L. et al., 1991, EMBO J. 10: 2867–2878; Wang, M. et al., 1994, Science 266: 117–119; Gaudino, G. et al., 1994, EMBO J. 13: 3524–3532).

The α chain of both factors contains a hairpin loop (HL) structure and four domains with a tangle-like structure named kringles (K1–K4; Nakamura T et al., 1989, Nature 342:440–443; Han, S. et al., 1991, Biochemistry 30: 9768–9780). The precursor also contains a signal sequence (LS) of 31 amino acids (in the case of HGF) or of 18 amino acids (in the case of MSP), removed in rough endoplasmic reticulum, which directs the neoformed peptide to the secretive pathway. The β chain contains a box with a sequence homologous to that typical of serine proteases, but it has no catalytic activity (Nakamura T et al., 1989, Nature 342:440–443; Han, S. et al., 1991, Biochemistry 30: 9768–9780). Both α and β chains contribute to the binding of the growth factor to the respective receptor (Met for HGF and Ron for MSP).

HGF and MSP polypeptides are able to induce a variety of biological effects besides cell proliferation. The main biological activities of these molecules are: stimulation of cell division (mitogenesis); stimulation of motility (scattering); induction of polarisation and cell differentiation; induction of tubule formation (branched morphogenesis); increase of cell survival (protection from apoptosis). The tissues that respond to HGF and MSP stimulation are those where cells express the respective Met (HGF) and Ron (MSP) receptors. The most important target tissues of these factors are epithelial cells of different organs, such as liver, kidney, lung, breast, pancreas and stomach, and some cells of the hematopoietic and nervous systems. A detailed review of the biological effects of HGF and MSP in the various tissues can be found in Tamagnone, L. & Comoglio, P., 1997, Cytokine & Growth Factor Re-views, 8: 129–142, Elsevier Science Ltd.; Zarnegar, R. & Michalopoulos, G., 1995, J. Cell Biol. 129: 1177–1180; Medico, E. et al., 1996, Mol. Biol. Cell, 7: 495–504; Banu, N. et al., 1996, J. Immunol. 156: S2933–2940.

In the case of HGF, the hairpin loop and the first two kringles are known to contain the sites of direct interaction with the Met receptor (Lokker NA et al., 1992, EMBO J., 11:2503–2510; Lokker, N. et al., 1994, Protein Engineering 7: 895–903). Two naturally-occurring truncated forms of HGF produced by some cells by alternative splicing have been described. The first one comprises the first kringle (NKI-HGF Cioce, V. et al., 1996, J. Biol. Chem. 271: 13110–13115) whereas the second one spans to the second kringle (NK2-HGF Miyazawa, K. et al., 1991, Eur. J. Biochem. 197: 15–22). NK2-HGF induces cell scattering, but it is not mitogenic as the complete growth factor is (Hartmann, G. et al., 1992, Proc. Natl. Acad. Sci. USA 89: 11574–11578). However, NK2-HGF regains mitogenic activity in the presence of heparin, a glucosaminoglycan that binds HGF through a domain contained in the first kringle and which is likely to induce dimerization of NK2-HGF (Schwall, R. et al., 1996, J. Cell Biol. 133: 709–718). Moreover NK2-HGF, being a partial agonist of Met, behaves as a competitive inhibitor of HGF as far as the mitogenic activity is concerned (Chan, A. et al., 1991, Science 254: 1382–1385). NK1-HGF has also been described to exert partial stimulation of Met and competitive inhibition of HGF mitogenic activity (Cioce, V. et al., 1996, J. Biol. Chem. 27: 13110–13115). Anyway, a truncated factor is endowed with an activity markedly lower than the recombinant factors described in the invention, as shown in example 3.

In the case of MSP, the interaction sites with the Ron receptor are less understood: some preliminary studies suggest a situation opposite of that of HGF, i.e. the β chain directly binds the receptor whereas the α chain would act stabilizing the complex (Wang MH et al., 1997, J. Biol. Chem. 272:16999–17004).

The therapeutical use of molecules such as HGF and MSP is potentially valuable in a wide range of pathologies (Abdulla, S., 1997, Mol. Med. Today 3: 233). Nevertheless, a number of technical as well as biological complications make the application of these molecules in clinics difficult. First of all, the pleiotropic character of these factors can causes poorly selective biological responses, which involve undesired side effects. For example, the use of HGF to prevent some side effects of the chemotherapeutic drug cisplatin has been proposed (Kawaida K et al., 1994, Proc. Natl. Acad. Sci. 91:4357–4361). Cancer patients treated with this drug can suffer kidney acute damage due to the cytotoxic action of cisplatin on proximal tubule epithelial cells. HGF is able to protect these cells against programmed death (apoptosis) induced by cisplatin, but at the same time it can induce an undesired proliferation of neoplastic cells. Other problems related to the pharmaceutical use of HGF and MSP are the necessity of their proteolytic activation and their stability, which causes technical problems. The NK1 and NK2 truncated forms of HGF do not require proteolytic activation, but they have a reduced biological activity.

SUMMARY OF THE INVENTION

The present invention provides recombinant molecules composed of a combination of structural domains derived from the α chains of HGF and/or MSP, which overcome the problems of the prior art molecules described above. The molecules of this invention are composed of two superdomains connected by a linker. Each superdomain is composed of a combination of the HL and K1–K4 domains of the α chain of HGF and/or MSP. These engineered factors induce selective biological responses, do not require proteolytic activation, are stable and are more active than the truncated forms of HGF described previously.

DETAILED DISCLOSURE OF THE INVENTION

The present invention relates to recombinant proteins (which will be hereinafter referred to indifferently as proteins, molecules, engineered or recombinant factors) characterised by a structure that comprises two superdomains, each consisting of a combination of HL and K1–K4 domains derived from the α chain of HGF and/or MSP, linked by a spacer sequence or a linker. In particular, the invention relates to proteins of general formula (I)

$$[A]\text{-}B\text{-}[C]\text{-}(D)_y \qquad (I)$$

in which
- [A] corresponds to the sequence $(LS)_m\text{-}HL\text{-}K1\text{-}(K2)_n\text{-}(K3)_o\text{-}(K4)_p$ wherein (the numbering of the following amino acids refers to the HGF and MSP sequences as reported in FIGS. 1 and 2, respectively):
  - LS is an amino acid sequence corresponding to residues 1–31 of HGF or 1–18 of MSP;
  - HL is an amino acid sequence derived from the α chain of HGF starting between residues 32–70 and ending between residues 96–127; or it is an amino acid sequence derived from the α chain of MSP starting between residues 19–56 and ending between residues 78–109;
  - K1 is an amino acid sequence derived from the α chain of HGF starting between residues 97–128 and ending between residues 201–205; or it is an amino acid sequence derived from the α chain of MSP starting between residues 79–110 and ending between residues 186–190;
  - K2 is an amino acid sequence derived from the α chain of HGF starting between residues 202–206 and ending between residues 283–299; or it is an amino acid sequence derived from the α chain of MSP starting between residues 187–191 and ending between residues 268–282;
  - K3 is an amino acid sequence derived from the α chain of HGF starting between residues 284–300 and ending between residues 378–385; or it is an amino acid sequence derived from the α chain of MSP starting between residues 269–283 and ending between residues 361–369;
  - K4 is an amino acid sequence derived from the α chain of HGF starting between residues 379–386 and ending between residues 464–487; or it is an amino acid sequence derived from the α chain of MSP starting between residues 362–370 and ending between residues 448–481;
  - m, n, o, p can be 0 or 1;
  - the sum n+o+p is an integer from 1 to 3 or 0, with the proviso that n≧o≧p;
- B is the sequence $[(X)_q Y]_r$, wherein X=Gly and Y=Ser, or Cys, or Met, or Ala;
  - q is an integer from 2 to 8;
  - r is an integer from 1 to 9;
- [C] corresponds to the sequence $HL\text{-}K1\text{-}(K2)_s\text{-}(K3)_t\text{-}(K4)_u$ wherein HL, K1–K4 are as defined above,
  - s, t, u are 0 or 1; the sum s+t+u is an integer from 1 to 3 or 0, with the proviso that s≧t≧u;
- D is the sequence W-Z, wherein W is a conventional proteolytic site, Z is any tag sequence useful for the purification and detection of the protein; y is 0 or 1.

Non-limiting examples of W are consensus sequences for enterokinase protease, thrombin, factor Xa and IgA protease.

Preferred proteins of general formula (I), are those in which: the HL domain is a sequence of HGF α chain ranging from amino acids 32 to 127, or a sequence of MPS α chain ranging from amino acids 19 to 98; the K1 domain is a sequence of HGF α chain ranging from amino acids 128 to 203, or a sequence of MPS α chain ranging from amino acids 99 to 188; the K2 domain is a sequence of HGF α chain ranging from amino acids 204 to 294, or a sequence of MPS α chain ranging from amino acids 189 to 274; the K3 domain is a sequence of HGF α chain ranging from amino acids 286 to 383, or a sequence of MPS α chain ranging from amino acids 275 and 367; the K4 domain is a sequence of HGF α chain ranging from amino acids 384 to 487, or a sequence of MPS α chain ranging from amino acids 368 and 477.

Among the possible combinations of the domains of general formula (I), the following (II) and (III) are preferred, concerning two recombinant factors named Metron Factor-1 and Magic Factor-1, respectively:

$$LS_{MSP}\text{-}HL_{MSP}\text{-}K1_{MSP}\text{-}K2_{MSP}$$
$$\text{-}L\text{-}HL_{HGF}\text{-}K1_{HGF}\text{-}K2_{HGF}\text{-}D$$
(Metron Factor-1) \qquad (II)

and $$LS_{HGF}\text{-}HL_{HGF}\text{-}K1_{HGF}\text{-}K2_{HGF}$$
$$\text{-}L\text{-}HL_{HGF}\text{-}K1_{HGF}\text{-}K2_{HGF}\text{-}D$$
(Magic Factor-1) \qquad (III)

For both molecules, L is a linker sequence $(Gly_4Ser)_3$, D is a tag sequence $Asp_4\text{-}Lys\text{-}His_6$.

For Metron Factor-1, $LS_{MSP}$ is the sequence 1–18 of MSP, $HL_{MSP}$ is the sequence 19–56 of MSP, $K1_{MSP}$ is the sequence 99–188 of MSP, $K2_{MSP}$ is the sequence 189–274 of MSP, $HL_{HGF}$ is the sequence 32–127 of HGF, $K1_{HGF}$ is the sequence 128–203 of HGF, $K2_{HGF}$ is the sequence 204–294 of HGF.

For Magic Factor-1, $HL_{HGF}$, $K1_{HGF}$, $K2_{HGF}$ are as defined above, $LS_{HGF}$ is the sequence 1–31 of HGF.

The hybrid molecules of the invention are prepared by genetic engineering techniques according to a strategy involving the following steps:

a) construction of DNA encoding the desired protein;

b) insertion of DNA in an expression vector;

c) transformation of a host cell with recombinant DNA (rDNA);

d) culture of the transformed host cell so as to express the recombinant protein;

e) extraction and purification of the produced recombinant protein.

The DNA sequences corresponding to HGF or MSP structural domains can be obtained by synthesis or starting from DNA encoding for the two natural factors. For example, screening of cDNA libraries can be carried out using suitable probes, so as to isolate HGF or MSP cDNA. Alternatively, HGF or MSP cDNA can be obtained by reverse transcription from purified mRNA from suitable cells.

cDNAs coding for the fragments of HGF and MSP β chains can be amplificated by PCR (Mullis, K. B. and Faloona, F. A., 1987, Methods in Enzymol. 155, 335–350), and the amplification products can be recombined making use of suitable restriction sites, naturally occurring in the factor sequences or artificially introduced in the oligonucleotide sequence used for the amplification.

In greater detail, one of the above mentioned strategies can be the following:

the portions of DNA encoding the LS, HL, K1, K2, K3 and K4 domains are amplificated by PCR from HGF or MSP cDNA and then recombined to obtain the hybrid sequences corresponding to [A] and [C]. Oligonucleotides recognising sequences located at the two ends of the domains to be amplificated are used as primers. Primers are designed so as to contain a sequence allowing recombination between the DNA of a domain and the adjacent one. Said recombination can be carried out by endonuclease cleavage and subsequent ligase reaction, or making use of the recombinant PCR method (Innis, N A et al., 1990, in PCR Protocols, Academic Press, 177–183).

The sequence encoding the domain B (linker) can be obtained by synthesis of a double chain oligonucleotide, which can be inserted between [A] and [C] using suitable restriction sites.

The resulting three fragments encoding for [A], [B] and [C] are then inserted in the correct sequence in a suitable vector. In this step it can be decided whether to add or not the domain D (tag), obtained by synthesis analogously to domain B, downstream fragment [C].

The recombinant expression vector can contain, in addition to the recombinant construct, a promoter, a ribosome binding site, an initiation codon, a stop codon, optionally a consensus site for expression enhancers.

The vector can also comprise a selection marker for isolating the host cells containing the DNA construct. Yeast or bacteria plasmids, such as plasmids suitable for *Escherichia Coli*, can be used as vectors, as well as bacteriophages, viruses, retroviruses, or DNA.

The vectors are cloned preferably in bacterial cells, for example in *Escherichia Coli*, as described in Sambrook J., 1989, Molecular Cloning, Cold Spring Harbor Laboratory Press, New York, and the colonies can be selected, for example, by hybridisation with radiolabelled oligonucleotide probes; subsequently, the rDNA sequence extracted from the positive colonies is determined by known methods.

The vector with the recombinant construct can be introduced in the host cell according to the competent cell method, the protoplast method, the calcium phosphate method, the DEAE-dextran method, the electric impulses method, the in vitro packaging method, the viral vector method, the micro-injection method, or other suitable techniques.

Host cells can be prokaryotic or eukaryotic, such as bacteria, yeasts or mammal cells, and they will be such as to effectively produce the recombinant protein.

After transformation, cells are grown in a suitable medium, which can be for example MEM, DMEM or RPMI 1640 in the case of mammal host cells.

The recombinant protein is secreted in the culture medium from which it can be recovered and purified with different methods, such as mass exclusion, absorption, affinity chromatography, salting-out, precipitation, dialysis, ultrafiltration.

A simple, rapid system for the production of the molecules of the invention is, for example, transient-expression in mammal cells.

Accordingly, the plasmid containing the recombinant DNA fragment, for example PMT2 (Sambrook, J. et al., 1989, Molecular Cloning, Cold Spring Harbor Laboratory Press), is transfected in suitable recipient cells, such as Cos7 (Sambrook, J. et al., supra) by the calcium phosphate technique or other equivalent techniques. Some days after transfection, the conditioned medium of the transfected cells is collected, cleared by centrifugation and analysed for its content in factor. For this analysis, antibodies directed against HGF or MSP, or against any tag sequence, can be used: the supernatant is immunoprecipitated and then analysed by western blot with the same antibody. The supernatant containing the recombinant factor can also be used directly for biochemical and biological tests. The protein can be purified, for example, using a poly-histidine tag sequence, by absorption on a nickel resin column and subsequent elution with imidazole.

The biochemical properties. of the recombinant factors of the invention were tested in connection with their ability to activate Met and Ron receptors.

Sub-micromolar concentrations of the factors have proved to induce phosphorylation in Met tyrosine in human epithelial cells A549, whereas they do not induce phosphorylation above basal values in cells expressing Ron. On the whole, the tests proved that the first two kringles of HGF maintain their ability to interact and to activate Met tyrosine kinase receptor, whereas the corresponding first two kringles of MSP are not sufficient for modulating the catalytic activity of the Ron receptor. However, the interaction with Ron, although at low affinity, can contribute to the recruitment of the factor at the cell surface, playing a similar role to low affinity receptors (of mature glycoprotein) which recruit the HGF intact molecule through the heparin-binding domain.

The molecules of the invention have a marked biological activity, measured by the scattering tests, and a protecting activity against cell apoptosis induced by cisplatin or etoposide.

In particular, the supernatant containing the recombinant factor has been found to promote scattering of epithelial cells of various nature even at nanomolar concentrations. In these tests, kidney epithelial cells (MDCK) or hepatocyte precursors (MLP29) were used.

In an in vitro experimental system, in which DNA fragmentation typical of apoptotic cells is evaluated by the TUNEL method (Gavrieli, Y. et al., 1992, J. Cell. Biol. 117, 493–501), the recombinant factors protect against apoptosis induced by chemotherapeutic drugs at levels comparable with HGF and remarkably higher than MSP. The engineered molecules proved to be active on human primary epithelial cells from proximal tubule (PTECs), on an immortalised PTECs line (Loc) and on the already cited murine hepatocytes MLP29.

Among the applications of the recombinant molecules of the invention, the following can be cited:

prevention of myelotoxicity; in particular they can be used for the expansion of marrow precursors, to increase proliferation of the hematopoietic precursors or to stimulate their entry in circle;

prevention of liver and kidney toxicity, and of mucositis following antineoplastic treatments; in particular the recombinant factors can be used to prevent toxicity (apoptosis) on differentiated cell elements of liver, kidney and mucosa of the gastroenteral tract, and to stimulate staminal elements of cutis and mucosas to allow the regeneration of germinative layers;

prevention of chemotherapeutic neurotoxicity.

In general, the proteins of the invention provide the following advantages, compared with the parent molecules HGF and MSP: they are smaller molecules with a more compact structure;

they are more stable and are produced in higher amounts;

they require no endoproteolytic cleavage for activation, which transforms the HGF and MSP precursors into the respective active forms;

they can be engineered in combinations of different functional domains, thereby modulating the biological effects, increasing the favourable ones and reducing those undesired (for example, protection from apoptosis versus cell proliferation).

The invention has to be considered also directed at amino acid and nucleotide sequences referred to formula (I), having modifications which can, for example, derive from degeneration of genetic code, without therefore modifying the amino acid sequence, or from the deletion, substitution, insertion, inversion or addition of nucleotides and/or bases according to all the possible methods known in the art.

Furthermore, the invention relates to the expression vectors comprising a sequence encoding for a protein of general formula (I), which can be plasmids, bacteriophages, vituses, retroviruses, or others, and to host cells containing said expression vectors, Finally, the invention relates to the use of the recombinant proteins as therapeutical agents, and to pharmaceutical compositions containing an effective amount of the recombinant proteins together with pharmacologically acceptable excipients.

DESCRIPTION OF THE FIGURES (In the following legends, -His located after the name of the parent factors, truncated or recombinant, or of the plasmids, means that the respective sequences contain a poly-histidine tag).

FIG. 1:
a) Nucleotide (SEQ ID NO: 17) and amino acid (SEQ ID NO: 18) sequence of human HGF (Gene Bank # M73239; Weidner, K. M., et al., 1991, Proc. Acad. Sci. USA, 88:7001–7005). In contrast to the cited reference, in the numbering used herein, nucleotide No. 1 is the first base of the initiation codon (the A of the first ATG). The first amino acid is the corresponding methionine. The cDNA untranslated regions at 5' and 3' are neither represented nor considered in the numbering.
b) Nucleotide (SEQ ID NO: 19) and amino acid (SEQ ID NO: 20) sequence of human MSP (Gene Bank # L11924; Yoshimura, T., et al., 1993, J. Biol. Chem., 268:15461–15468). In contrast to the cited reference, in the numbering used herein nucleotide No. 1 is the first base of the initiation codon (the A of the first ATG). The first amino acid is the corresponding methionine. The cDNA untranslated regions at 5' and 3' are neither represented nor considered in the numbering.

FIG. 2:
a) Molecular structure of Metron Factor-1. The leader sequence is removed from the cells used for the production before secretion and is therefore absent in the mature molecule. The poly-histidine tag can be removed by digestion with the protease enterokinase.
b) Nucleotide (SEQ ID NO: 21) and amino acid (SEQ ID NO: 4) sequence of Metron-Factor-1. The nucleotide sequence starts with the EcoRI site and terminates with the SalI site (first six bases and last six bases, respectively). The initiation codon (ATG) and the stop codon (TAG) are underlined.

Figure 3A:
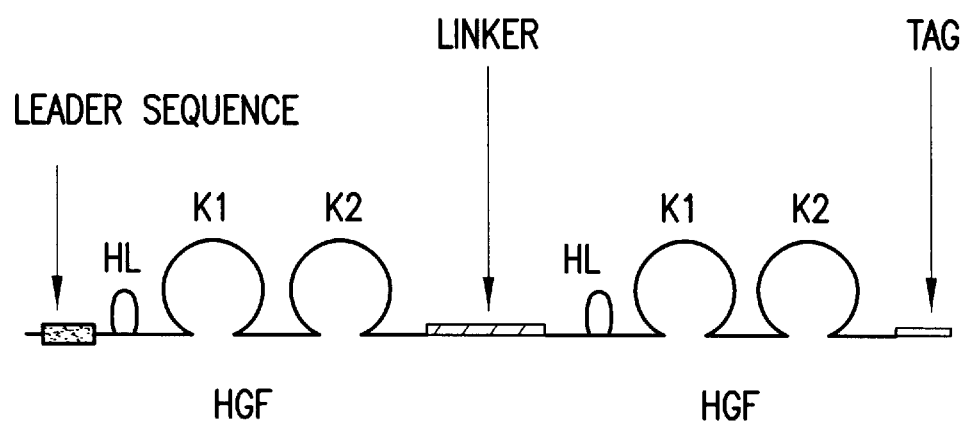

FIG. 3:
a) Molecular structure of Magic Factor-1. The leader sequence is removed from the cells used for the production before secretion and is therefore absent in the mature molecule. Poly-histidine tag can be removed by digestion with the protease enterokinase.
b) Nucleotide (SEQ ID NO: 22) and amino acid (SEQ ID NO: 2) sequence of Magic Factor-1. The nucleotide sequence starts with the SalI site (first six bases and last six bases, respectively). The initiation codon (ATG) and the stop codon (TAG) are underlined.

FIG. 4:
Production of Metron-F-1 by transient transfection of mammal cells. The conditioned supernatants from BOSC cells transfected with the control plasmid (CTRL) or with pRK7-Metron F-1-His were immunoprecipitated with an anti-MSP polyclonal antibody and detected by western blot with the same antibody.

FIG. 5:
Quantitation of the recombinant proteins by western blot. (A) The proteins were absorbed on Sepharose-A-heparin beads and detected with an anti-poly-histidine monoclonal antibody. (B) The proteins were immunoprecipitated with an anti-MSP polygonal antibody and detected with an anti-poly-histidine monoclonal antibody.

Figure 6:
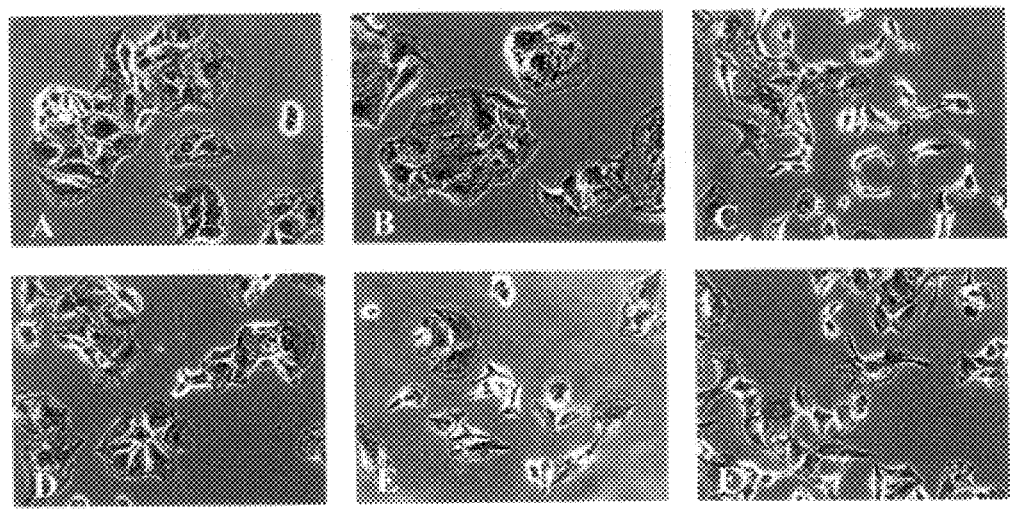

FIG. 6:
Scattering test carried out on kidney epithelial cells (MDCK) using the recombinant proteins prepared by transient transfection. The protein content was quantified by western blot (see FIG. 5). (A) non-stimulated cells; (B) cells stimulated with control supernatant; (C) cells stimulated with HGF-His; (D) cells stimulated with NK2-HGF-His; (E) cells stimulated with Metron Factor-1; (F) cells stimulated with Magic Factor-1.

Figure 7:
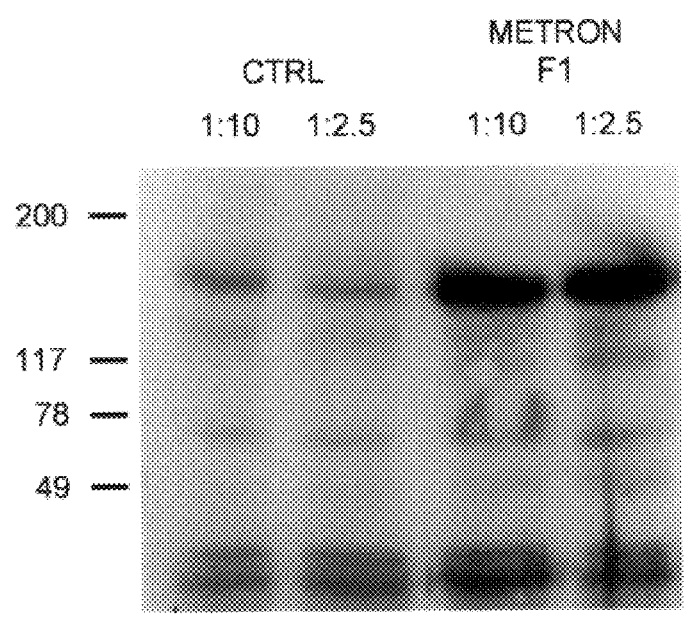

FIG. 7:
Activation (phosphorylation) of Met receptor by the hybrid factor Metron Factor-1. Human epithelial cells (A549) were stimulated with supernatants conditioned from BOSC cells transfected with the control plasmid (CTRL) or with pRK7-Metron-F-1-His (METRON F-1) at the indicated dilutions. Cell lysates from the stimulated cells were immunoprecipitated with an anti-Met monoclonal antibody and detected by western blot with an anti-phosphotyrosine monoclonal antibody.

Figure 8:
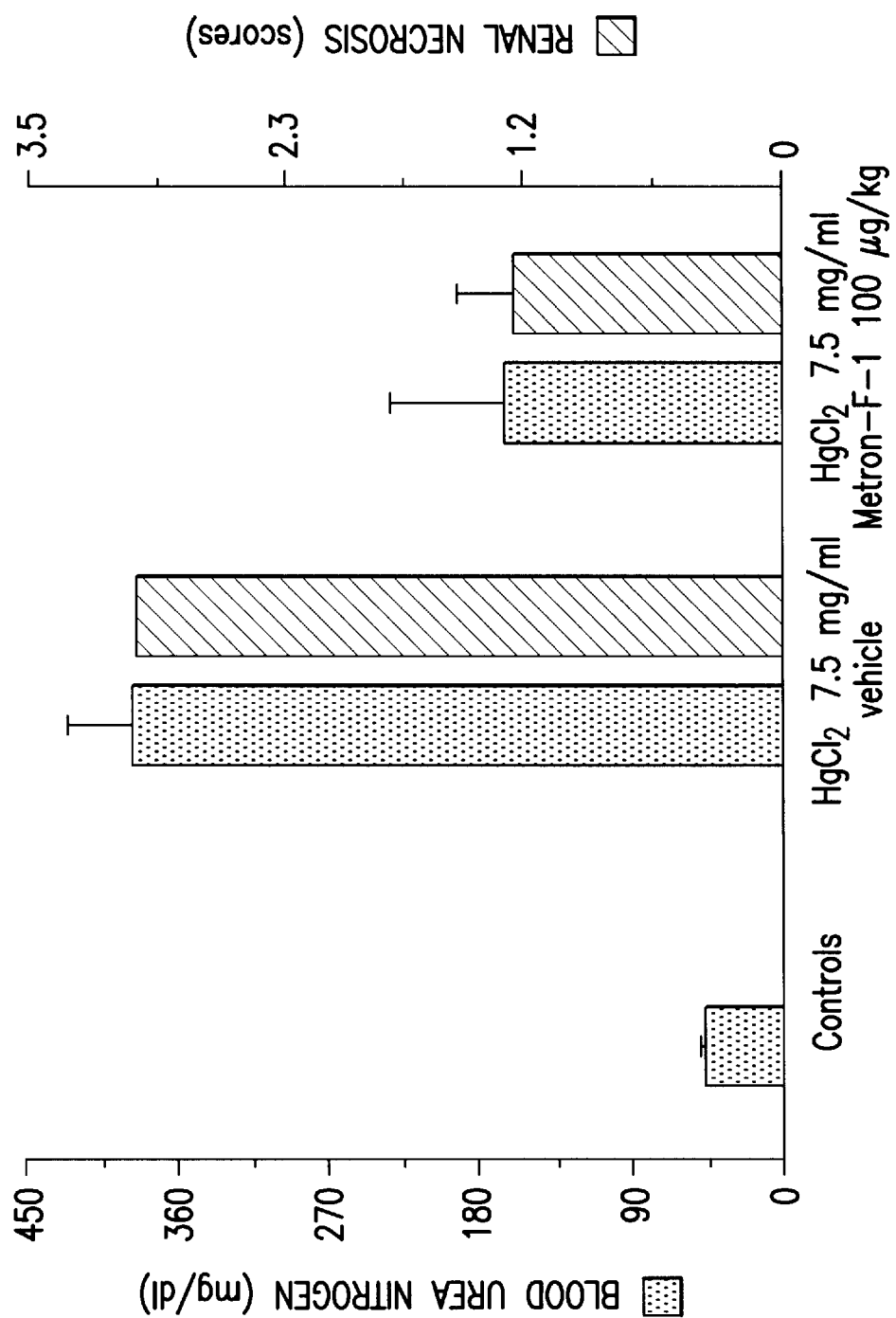

FIG. 8:
Protective effect of Metron-F-1 against acute renal failure induced by $HgCl_2$ in vivo. Balb-c mice were injected i.v. with Metron-F-1 or vehicle at 0.5 h before and 6, 12, 24, 36 and 48 h after HgCl$_2$ i.v. administration. BUN and histological evaluation of renal necrosis were measured at 72 h.

Data expressed as mean+e.s. of 7 animals/group (BUN) or 3 animals/group (histology).

The following examples illustrate in greater detail the invention.

EXAMPLE 1a

Preparation of the Recombinant Construct Encoding Metron Factor-1

HGF cDNA was obtained by the RT-PCR technique (Reverse Transcriptase PCR; in: Innis, M. A., et al., 1990, PCR Protocols, Academic Press, 21–27) from a human lung fibroblast cell line (MRC5; Naldini, L. et al., 1991, EMBO J. 10: 2867–2878). MSP cDNA was obtained with the same technique from human liver (Gaudino, G., et al., 1994, EMBO J. 13: 3524–3532).

The fragment corresponding to MSP LS-HL-K1-K2 was amplified by PCR using MSP cDNA as template and the following oligonucleotides as primers:

P1 (sense) (SEQ ID NO: 5)

5' CGCGCGGAATTCCACCATGGGGTGGCTCCCACTCCT 3'

P2 (antisense) (SEQ ID NO: 6)

5' CGCGCGCTCGAGGCGGGGCTGTGCCTCGGACCCGCA 3' in which the underlined palindromic sequences are the restriction sites for the enzymes EcoRI (oligonucleotide P1) and XhoI (oligonucleotide P2). The PCR product was digested with the restriction enzymes EcoRI and XhoI and then purified by electrophoresis on agarose gel.

The fragment corresponding to HL-K1–K2 of HGF was amplified by PCR using HGF cDNA as template and the following oligonucleotides as primers:

P3 (sense) (SEQ ID NO: 7)

5' CGCGCGTCTAGAGGGACAAAGGAAAAGAAGAAATAC 3'

P4 (antisense) (SEQ ID NO: 8)

5' CGCGCGAAGCTTTGTCAGCGCATGTTTTAATTGCAC 3' in which the underlined palindromic sequences are the restriction sites for the enzymes XbaI (oligonucleotide P3) and HindIII (oligonucleotide P4). The PCR product was digested with the restriction enzymes XbaI and HindIII and then purified by electrophoresis on agarose gel.

For the linker sequence, the following partially complementary oligonucleotides were synthesised, and were subsequently annealed to obtain a double strand DNA fragment with sticky ends:

P5 (sense) (SEQ ID NO: 9)

5' TCGAGGGCGGTGGCGGTTCTGGTGGCGGTGGCTCCGGCGGTGGCGGTTCT 3'

P6 (antisense) (SEQ ID NO: 10)

5' CTAGAGAACCGCCACCGCCGGAGCCACCGCCACCAGAACCGCCACCGCCC 3' in which the underlined bases are the sequences compatible with the restriction sites for the enzymes XhoI (oligonucleotide P5) and XbaI (oligonucleotide P6).

The resulting three DNA fragments were subcloned in the EcoRI-HindIII sites of the expression vector pRK7 (Gaudino, G., et al., 1994, EMBO J. 13: 3524–3532), to obtain the recombinant plasmid pRK7-Metron-F-1, containing all the components of Metron Factor-1 except the tag sequence.

For the insertion of the tag sequence, the following partially complementary oligonucleotides were synthesised, and were subsequently annealed to obtain a double strand DNA fragment with sticky ends:

P7 (sense) (SEQ ID NO: 11)

5' AGCTGACGACGACGACCACCACCACCACCACCACTAGGGTCGAC 3'

P8 (antisense) (SEQ ID NO: 12)

5' AGCTGTCGACCCTAGTGGTGGTGGTGGTGGTGGTGTTTGTCGTCGTCGTC 3' in which the underlined bases are compatible with the HindIII restriction site and the boxed palindromic sequences are the consensus sequences for the enzyme SalI. The resulting double strand DNA fragment was inserted in the restriction site HindIII of the recombinant plasmid obtained at the previous step (destroying the HindIII site and creating the SalI site), to obtain the plasmid pRK7-Metron-F-1-His.

EXAMPLE 1b

Production of Metron Factor-1

The expression vector pRK7 contains a promoter of human cytomegalovirus immediate-early gene (CMV) and an episomal replication origin site of the DNA virus SV40. Therefore, this plasmid is particularly suitable for the expression of proteins in cells expressing the large T antigen of the virus SV40, such as kidney epithelial BOSC cells (Sambrook, J. et al., 1989, Molecular Cloning, Cold Spring Harbor Laboratory Press). Metron Factor-1 can then be produced by transient transfection of plasmid pRK7-Metron F-1-His in BOSC cells.

For transfection, $10^6$ cells are seeded at day 0 in a 100 mm plate in 90% Dulbecco's Modified Eagle Medium (DMEM)-10% bovine calf serum (10 ml/plate). At day 1, cells are transfected with 10 μg/plate of pRK7-Metron-F-1-His by lipofection, using the protocol provided by the lipofectin producer (Gibco-BRL). At day 2, the DNA-containing medium is substituted by fresh medium with low content in serum (99.5% DMEM-0.5% bovine calf serum). At day 4 (48 hours after the end of the transfection), the medium is collected, cleared by centrifugation, and analysed for its content in Metron Factor-1.

This analysis can be carried out in different ways. For example, the recombinant protein present in the cleared supernatant can be immunoprecipitated with an anti-MSP antibody and then detected by western blot with the same antibody (FIG. 4). In the example shown in FIG. 4, 500 μl of supernatant (cleared by centrifugation, buffered in 25 mM HEPES and added with a protease inhibitors cocktail) were immunoprecipitated (2 hours at 4° C.) with 20 μl of Sepharose-A beads (Pharmacia) covalently conjugated with 2 μl of anti-MSP polyclonal antibody. The beads pellet was washed 3 times with 500 μl of washing buffer (20 mM HEPES pH 7.4; 150 mM NaCl; 0.1% Triton X-100; 10% glycerol) and heated at 90° C. for 2 minutes in 100 ul of Laemmli buffer. Eluted proteins were separated by SDS-PAGE on 8% BIS-acrylamide gel, transferred onto membrane (Hybond-C; Amersham) and analysed by western blot. For this analysis, the same rabbit serum used for immunoprecipitation was employed as primary antibody with a 1:1000 dilution and protein A conjugated with peroxidase (Amersham) was used as secondary antibody. Protein A was detected by ECL (Amersham) following the protocol provided by the producer.

Alternatively, the recombinant protein can be partially purified by adsorption on Sepharose-A beads conjugated with heparin and subsequent analysis by western blot using antibodies directed to poly-histidine tag (FIG. 5).

In the example shown in FIG. 5, the Sepharose-A-heparin beads (20 µl; Pierce) were incubated (4 hours at 4° C.) with 500 µl of supernatant (cleared by centrifugation, buffered in 25 mM HEPES and added with a protease inhibitors cocktail) in the presence of 500 mM NaCl, washed with suitable buffer (500 mM NaCl; 20 mM HEPES pH 7.4; 0.1% Triton X-100; 10% glycerol) and heated at 90° C. for 2 minutes in 100 µl Laemmli buffer. Eluted proteins were separated by SDS-PAGE on 8% bis-acrylamide gel, transferred onto membrane (Hybond-C; Amersham) and analysed by western blot. For this analysis, a mouse monoclonal antibody to poly-histidine (Invitrogen) diluted 1:5000 was used as primary antibody and an anti-mouse IgG ovine antibody conjugated with peroxidase (Amersham) was used as secondary antibody. The secondary antibody was detected by ECL (Amersham) following the protocol provided by the producer.

The procedure of adsorption on heparin beads can also be used as protocol for the semi-purification of the recombinant protein. Furthermore, the molecule can additionally be purified making use of the poly-histidine affinity to heavy metals such as nickel. The protein containing poly-histidine tag can be adsorbed on a nickel resin column (invitrogen) and subsequently eluted with imidazole (the detailed protocol is provided by the manufacturer).

EXAMPLE 1c

METRON-F-1 Production in Insect Cells

The cDNA encoding for Metron-F1 was subcloned in a suitable expression vector (p-FASTBAC) to generate a recombinant plasmid containing the Metron-F1 gene (p-FASTBAC-Metron). A competent E. Coli strain (DH10 Bac) was transformed with p-FASTBAC-Metron to generate BACMID DNA. The DNA of positive colonies was isolated and checked by PCR to show the correct integration of the expression vector. Subsequently, the DNA from three clones was transfected into Sf9 insect cells with CellFECTIN reagent to produce virus particles. Virus titer was tested by a plaque assay. Single plaques were isolated and used for further propagation of the baculovirus. Viral stock was subsequently expanded in insect cells to scale up METRON-F-1 production. To verify protein expression, insect cells were infected with a multiplicity of infection (MOI) of 1 in a small-scale reactor. Samples of supernatants were analysed by SDS-PAGE followed by western blotting.

To produce amounts adequate for in vivo testing, insect cells were propagated in a 2.5-Liter stirred tank bioreactor. Cells were grown to a cell density of 1.106 ml$^{-1}$ before they were infected with a MOI of 1. Cell suspension was harvested 3 days post infection. The supernatant containing the recombinant protein was separated by centrifugation. The presence of Metron F-1 in the supernatant was proved by SDS-PAGE followed by western blotting. Metron F-1 was pre-purified by a dual step affinity chromatography on heparin sepharose (heparin-Hi Trap, Pharmacia) at 6° C. For in vivo testing or for further purification steps, the eluted fractions containing Metron F-1 were desalted by Sephadex G-25 chromatography (PD-10 or HiPrep 26/10, Pharmacia). Metron F-1 was further purified by chromatography on HisTrap columns (Pharmacia) and eluted by an imidazole gradient (0–0.5 M) using either a low-pressure system (Econo System, BIO-RAD) or an FPLC system (Pharmacia). Metron F-1 was eluted at an imidazole concentration of about 0.15 M. For in vivo testing, the eluted fractions containing Metron F-1 were freed of imidazole by Sephadex G-25 chromatography as already described, using the buffer to be used for animal treatment.

EXAMPLE 2a

Preparation of the Recombinant Construct Encoding for Magic Factor-1

HGF cDNA and the plasmid pRK7-Metron-F-1-His described above were used as starting DNA. The fragment corresponding to LS-HL-K1–K2 of HGF was amplificated by PCR using HGF cDNA as template and the following oligonucleotides as primers:

P9 (sense) (SEQ ID NO: 13)

5' CGCGCG GGATCCGCCAGCCCGTCCAGCAGCACCATG 3'

P10 (antisense) (SEQ ID NO: 14)

5' CGCGCG AAGCTTTGTCAGCGCATGTTTTAATTGCAC 3' in which the underlined palindromic sequences are the restriction sites for the enzymes BamHI (oligonucleotide P9) and HindIII (oligonucleotide P10). The PCR product was digested with the restriction enzymes BamHI and HindIII and then purified by electrophoresis on agarose gel.

For the linker, the following partially complementary oligonucleotides were synthesized, and subsequently annealed to obtain a double strand DNA fragment with sticky ends:

P11 (sense) (SEQ ID NO: 15)

5' AGCTTCGGGCGGTGGCGGTTCTGGTGGCGG TGGCTCCGGCGGTGGCGGTTCT 3'

P12 (antisense) (SEQ ID NO: 16)

5' CTAGAGAACCGCCACCGCCGGAGCCAC CGCCACCACAACCGCCACCGCCCGA 3' in which the underlined bases are the sequences compatible with the restriction sites for the enzymes HindIII (oligonucleotide P11) and XbaI (oligonucleotide P12). The fragment resulting by PCR and the double strand linker sequence were inserted in the plasmid pRK7-Metron-F-1-His in place of the fragment EcoRI-XbaI by means of an EcoRI-BamHI adapter, to obtain the plasmid pRK7-Magic-F-1-His.

EXAMPLE 2b

Production of Magic Factor-1

Magic Factor-1 is produced on a small scale by transient transfection of BOSC cells analogously to what described for Metron Factor-1. Semi-purification is performed by adsorption on Sepharose-A beads conjugated with heparin followed by Western blot analysis using anti-poly-histidine antibodies (FIG. 5).

EXAMPLE 3

Biological Activity (Scattering) on Epithelial Cells

The biological activity of recombinant HGF, NK2-HGF, Metron Factor-1 and Magic Factor-1 was tested by a "scatter" assay on MDCK epithelial cells. For this functional test, cells are plated at day 0 in 96-well plates ($10^3$ cells/well) in 90% DMEM—10% bovine calf serum. At day 1 the medium is substituted with fresh medium buffered with 50 mM HEPES pH 7.4 and the supernatant containing the recombinant protein is added at different dilutions. At day 2 cells are washed with DPBS (Dulbecco's Phosphate Buffered Saline), fixed in 11% glutaraldehyde, stained with a Crystal-Violet solution and analysed by microscopy. The scattering activity is evaluated observing the morphology of the colonies, which are clustered in the negative control (non-stimulated cells or stimulated with supernatant containing no factors) whereas they are dispersed in the positive control (HGF-His). The morphology of the cells themselves also varies upon stimulation: in fact, as it can be observed in FIG. 6, cells stimulated with HGF-His and Metron Factor-1 have a more oblong, spindle-shaped form, characterised by protrusions of the cell membrane called pseudopodes. These morphological variations are the consequence of factor-induced activation of a genetic program involving the modification of a series of cellular parameters, such as digestion of cell matrix by specific proteases and increase in motility.

The Table summarises the results of different tests, obtained with factors HGF, NK2-HGF, Metron Factor-1 and Magic Factor-1 on MDCK cells. The scattering units reported indicate the maximum dilution of the conditioned supernatant containing the factor, at which motogenic activity could be observed. Values are normalised for the protein content determined by western blotting as described above (see FIG. 5). These data indicate that the hybrid factors Metron Factor-1 and Magic Factor-1 have a scattering activity approximately three magnitudes higher than that of the NK2-HGF-His truncated form and one magnitude higher than that of HGF-His parental factor.

|  | HGF-his | NK2-his | Metron F-1 | Magic Factor-1 |
|---|---|---|---|---|
| Scatter units | 900 ± 29 | 6 ± 5 | 5500 ± 1532 | 7600 ± 150 |

Table. Scattering activity of factors HGF-His, NK2-HGF-His Metron Factor-1 measured on kidney epithelial cells (MDCK). The scattering units reported indicate the maximum dilution of the conditioned supernatant containing the factor, at which a motogenic activity can be observed. Values are normalised for the protein content determined by western blotting.

EXAMPLE 4a

Test for the Evaluation of Protection Against Programmed Cell Death (Apoptosis)

One of the most characterised side effect of the chemotherapeutic drug cisplatin is the induction of programmed cell death (apoptosis) of epithelial cells of the proximal tubule, which leads to acute renal failure (ARF). Thus, a factor that protects against cisplatin-induced cytotoxicity is highly desirable. An in vitro functional test has been used, which allows to evaluate the percentage of cisplatin-treated apoptotic cells in the presence or in the absence of a survival factor. This system utilises a cell line (LOC) derived from epithelial cells of human kidney proximal tubule, immortalised by ectopic expression of SV40 large T antigen. For the functional test, cells are plated at day 0 in 96-well plates ($10^3$ cells/well) in 90% DMEM—10% bovine calf serum. At day 1, the medium is substituted with medium containing 0.5% bovine calf serum buffered with 50 mM HEPES pH 7.4, which is added with different dilutions of the supernatant containing the recombinant factor. Cells are incubated with these factors for 6 hours, and then further incubated in the presence of 10 μg/ml cisplatin. At day 2, cells are washed with DPBS and the percentage of apoptotic cells is evaluated by the TUNEL technique (Boehringer Mannheim). The same kind of tests can be performed using primary cultures of human epithelial cells of kidney proximal tubule (PTEC). These tests proved that Metron Factor-1 and Magic Factor-1 have protecting activity against cisplatin-induced programmed cell death.

EXAMPLE 4b

Protection Against Cisplatin-induced Cytotoxicity by Transient Gene Delivery of Metron Factor-1 and Magic Factor-1

The protective effect of Metron F-1 and Magic F-1 against cisplatin-induced cytotoxicity was further demonstrated by a transient gene delivery approach. Simian kidney epithelial cells (COS) were transfected with a control empty vector, an expression vector for Metron F-1, or an expression vector for Magic F-1. Following transfection, cells were treated for 16 hours with cisplatin (20 μg/ml) and the percentage of surviving cells in each transfection was determined. Cisplatin treatment was calibrated to cause the death of approximately 20% of the cells in the negative control. Ectopic expression of Metron F-1 or Magic F-1 increased the survival rate to about 92.3% and 94.0%, respectively.

EXAMPLE 5

Activation of the Met receptor by Metron Factor-1 and Magic Factor-1

The ability of Metron Factor-1 and Magic Factor-1 to activate the Met receptor was tested by analysing the ability of the recombinant factors to induce tyrosine phosphorylation of Met in human epithelial cells (A549). For this analysis, A549 cells at 90% confluence in a 100 mm petri dish were stimulated for 10 minutes with 1 ml of conditioned supernatant containing Metron Factor-1, Magic Factor-1 or no factor (as negative control) diluted 1:2.5 or 1:10 in DMEM. After stimulation, cells were washed in ice with PBS, lysated in 200 μl of lysis solution (1% Triton X-100, 5 mM EDTA, 150 mM NaCl, 20 mM Tris-HCl pH 7.4), added with a cocktail of protease inhibitors, immunoprecipitated for 2 hours at 4° C. with 10 μl of Sepharose-A beads covalently conjugated with an anti-Met monoclonal antibody (Naldini, L. et al., 1991, EMBO J. 10: 2867–2878), washed 3 times in the same lysis solution, and heated at 90° C. for 2 minutes to elute the absorbed proteins. These were separated by SDS-PAGE on a 8% BIS-acrylamide gel, transferred onto a membrane (Hybond-C; Amersham) and analysed by western blot. A mouse monoclonal antibody against phosphotyrosine (UBI) diluted 1:10000 was used as primary antibody and an anti-mouse IgG ovine antibody conjugated with peroxidase (Amersham) was used as secondary antibody. The secondary antibody was detected by ECL (Amersham) following the protocol provided by the manufacturer. This analysis revealed that Metron F-1 and Magic F-1 potently activate the Met receptor (FIG. 7).

EXAMPLE 6

Protection Against Chemotherapy-induced Renal Failure by Metron Factor-1 In vivo Metron-F-1 was tested in a model of nephrotoxicity in Balb-c mice. The method used was substantially as described (Kawaida K et al., 1994, Hepatocyte growth factor prevents acute renal failure and accelerates renal regeneration in mice, Proc. Natl. Acad. Sci. 91:4357–4361). Briefly, renal failure was induced in male Balb-c mice weighing 20–25 g by an i.v. injection of 7.5 mg/kg of $HgCl_2$ (7 animals/group). Renal damage was assessed by analysis of Blood Urea Nitrogen (BUN) and by histological evaluation, 72 h after $HgCl_2$ injection. Metron-F-1 was dissolved in 0.2 M NaCl, containing 0.01% Tween 80 and 0.25% human serum albumin and administered i.v. (100 μg/kg in a posological volume of 6.6 ml/kg) 0.5 h before and 6, 12, 24, 36 and 48 h after $HgCl_2$ injection. Controls animals were treated with the same amount of vehicle according to the same scheme.

Metron-F-1 significantly prevented the onset of acute renal failure induced by $HgCl_2$, evaluated in terms of BUN (FIG. 8). BUN values were closely paralleled by the histological findings, scored by an independent investigator.

In the following sequence listing:
SEQ. ID. NO. 1: Magic F-1 DNA coding sequence;
SEQ. ID. NO. 2: Magic F-1 amino acid sequence;
SEQ. ID. NO. 3: Metron F-1 DNA coding sequence;
SEQ. ID. NO. 4: Metron F-1 amino acid sequence.

What is claimed is:

1. A recombinant protein comprising two super domains, separated by a spacer sequence (linker), obtained by combining the HL and K1–K4 domains of HGF and/or MSP α chains, according to general formula (I):

[A]-B-[C]-(D)$_y$    (I)

in which

[A] corresponds to the sequence (LS)$_m$-HL-K1-(K2)$_n$ wherein:
  LS comprises amino acid residues 1–18 of MSP (SEQ ID NO:20);
  HL comprises an amino acid sequence starting between residues 32–70 of the HGF α chain (SEQ ID NO:18) and ending between residues 96–127 of the identical chain or an amino acid sequence starting between residues 19–56 of the MSP α chain (SEQ ID NO:20) and ending between residues 78–109 of the identical chain;
  K1 comprises an amino acid sequence starting between residues 97–128 of the HGF α chain (SEQ ID NO:18) and ending between residues 201–205 of the identical chain or an amino acid sequence starting between residues 79–110 of the MSP α chain (SEQ ID NO:20) and ending between residues 186–190 of the identical chain;
  K2 comprises an amino acid sequence starting between residues 202–206 of HGF α chain (SEQ ID NO:18) and ending between residues 283–299 of the identical chain or an amino acid sequence starting between residues 187–191 of MSP α chain (SEQ ID NO:20) and ending between residues 268–282 of the identical chain;
  m and n are 0 or 1;
B is the sequence [(X)$_q$Y]$_r$, wherein X=Gly and Y=Ser, or Cys, or Met, or Ala;
  q is an integer from 2 to 8;
  r is an integer from 1 to 9;

[C] corresponds to the sequence HL-K1-(K2)$_s$ wherein HL, K1, and K2 are as defined above,
  s is 0 or 1;
D is the sequence W-Z, wherein W is a conventional proteolytic site, Z is any tag sequence useful for the purification and detection of the protein; and y is 0 or 1.

2. The recombinant protein according to claim 1, wherein:
  HL comprises amino acids 32 to 127 of the HGF α chain (SEQ ID NO:18), or amino acids 19 to 98 of the MPS α chain (SEQ ID NO:20);
  K1 comprises amino acids 128 to 203 of the HGF α chain (SEQ ID NO:18), or amino acids 99 to 188 of the MPS α chain (SEQ ID NO:20); and
  K2 comprises amino acids 204 to 294 of the HGF α chain (SEQ ID NO:18), or amino acids 189 to 274 of the MPS α chain (SEQ ID NO:20).

3. The recombinant protein according to claim 1 of formula (II):

LS$_{MSP}$-HL$_{MSP}$-K1$_{MSP}$-K2$_{MSP}$-L-HL$_{HGF}$-K1$_{HGF}$-K2$_{HGF}$-D    (II)

wherein LS$_{MSP}$ comprises amino acids 1–18 of MSP (SEQ ID NO:20), HL$_{MSP}$ comprises amino acids 19–56 of MSP (SEQ ID NO:20), K1$_{MSP}$ comprises amino acids 99–188 of MSP (SEQ ID NO:20), K2$_{MSP}$ comprises amino acids 189–274 of MSP, HL$_{HGF}$ comprises amino acids 32–127 of HGF, K1$_{HGF}$ comprises amino acids 128–203 of HGF, K2$_{HGF}$ comprises amino acids 204–294 of HGF, L comprises the sequence (Gly$_4$Ser)$_3$, D comprises the sequence Asp$_4$-His$_6$.

4. A therapeutic agent comprising the recombinant protein of claim 1.

5. A pharmaceutical composition comprising an effective amount of the recombinant protein of claim 1 in combination with pharmacologically acceptable excipients.

* * * * *